(12) United States Patent
Selvitelli et al.

(10) Patent No.: US 9,107,594 B2
(45) Date of Patent: *Aug. 18, 2015

(54) ECG ELECTRODE CONNECTOR

(71) Applicant: Covidien LP, Mansfield, MA (US)

(72) Inventors: David Selvitelli, Suffield, CT (US);
Peter Meyer, Shrewsbury, MA (US);
Peter Yu, Bao An (CN)

(*) Notice: Subject to any disclaimer, the term of this patent is extended or adjusted under 35 U.S.C. 154(b) by 0 days.

This patent is subject to a terminal disclaimer.

(21) Appl. No.: 14/324,380

(22) Filed: Jul. 7, 2014

(65) Prior Publication Data

US 2014/0322945 A1 Oct. 30, 2014

Related U.S. Application Data

(63) Continuation of application No. 14/041,471, filed on Sep. 30, 2013, now Pat. No. 8,795,004, which is a continuation of application No. 13/785,713, filed on Mar. 5, 2013, now Pat. No. 8,690,611, which is a (Continued)

(51) Int. Cl.
*H01R 13/629* (2006.01)
*A61B 5/04* (2006.01)
(Continued)

(52) U.S. Cl.
CPC ................ *A61B 5/04* (2013.01); *A61B 5/0416* (2013.01); *A61B 5/04286* (2013.01);
(Continued)

(58) Field of Classification Search
CPC ............. A61B 5/0416; A61B 5/04286; A61B 2562/227; A61B 5/04; H01R 13/6277; H01R 13/62933; H01R 2101/00; H01R 2201/12; H01R 24/20; Y10S 439/909
USPC ......... 439/729, 261, 268, 859, 909, 835, 838; 607/152; 600/372
See application file for complete search history.

(56) References Cited

U.S. PATENT DOCUMENTS 3,606,881 A 9/1971 Woodson
3,752,151 A 8/1973 Robichaud
(Continued)

FOREIGN PATENT DOCUMENTS

CN 101491437 A 7/2009
CN 101491438 A 7/2009
(Continued)

OTHER PUBLICATIONS

Partial Search Report dated Jun. 5, 2014 for Application No. PCT/US2014/027328 6 pages.
(Continued)

*Primary Examiner* — Edwin A. Leon
(74) *Attorney, Agent, or Firm* — Lisa E. Winsor, Esq.

(57) ABSTRACT

Shown is an ECG electrode lead wire connector which provides improved electrical and mechanical coupling of the ECG electrode press stud to the lead wire, provides enhanced ergonomics to the clinician, and may alleviate patient discomfort associated with the attachment and removal of ECG leads. The connector may be engaged and disengaged with little or no force imparted to the patient or the ECG pad, which significantly minimizes the risk of inadvertent dislodgement of the pad. In one embodiment the shown connector provides a thumb cam lever which affirmatively engages the press stud to the connector, and provides tactile feedback to the clinician that the connector is properly engaged. In other embodiments, the connector provides a pushbutton to enable the clinician to easily engage and disengage the connector from the ECG stud. The shown connectors may also decrease clinician fatigue, and may provide more reliable ECG results.

13 Claims, 15 Drawing Sheets

Related U.S. Application Data continuation of application No. 13/443,096, filed on Apr. 10, 2012, now Pat. No. 8,408,948, which is a continuation of application No. 13/182,656, filed on Jul. 14, 2011, now Pat. No. 8,152,571, which is a continuation of application No. 12/330,550, filed on Dec. 9, 2008, now Pat. No. 8,038,484.

(60) Provisional application No. 61/012,825, filed on Dec. 11, 2007.

(51) Int. Cl.
  A61B 5/0416    (2006.01)
  A61B 5/0428    (2006.01)
  H01R 13/627    (2006.01)
  H01R 24/20     (2011.01)
  H01R 101/00    (2006.01)

(52) U.S. Cl.
  CPC ..... *H01R 13/6277* (2013.01); *H01R 13/62933* (2013.01); *A61B 2562/227* (2013.01); *H01R 24/20* (2013.01); *H01R 2101/00* (2013.01); *H01R 2201/12* (2013.01); *Y10S 439/909* (2013.01)

(56) References Cited

U.S. PATENT DOCUMENTS

| | | | |
|---|---|---|---|
| 3,805,769 | A | 4/1974 | Sessions |
| 3,828,766 | A | 8/1974 | Krasnow |
| 3,829,826 | A | 8/1974 | Brown et al. |
| 3,842,394 | A | 10/1974 | Bolduc |
| 3,868,946 | A | 3/1975 | Hurley |
| 3,888,240 | A | 6/1975 | Reinhold, Jr. et al. |
| 3,895,635 | A | 7/1975 | Justus et al. |
| 3,901,218 | A | 8/1975 | Buchalter |
| 3,997,225 | A | 12/1976 | Horwinski |
| 3,998,213 | A | 12/1976 | Price |
| 4,027,664 | A | 6/1977 | Heavner, Jr. et al. |
| 4,034,854 | A | 7/1977 | Bevilacqua |
| 4,077,397 | A | 3/1978 | Ellis et al. |
| 4,112,941 | A | 9/1978 | Larimore |
| 4,166,465 | A | 9/1979 | Esty et al. |
| 4,220,390 | A | 9/1980 | Cobaugh et al. |
| 4,303,293 | A | 12/1981 | Grunwald |
| D263,167 | S | 2/1982 | Stone |
| 4,353,372 | A | 10/1982 | Ayer |
| 4,365,634 | A | 12/1982 | Bare et al. |
| 4,498,480 | A | 2/1985 | Mortensen |
| 4,674,817 | A | 6/1987 | Olms |
| 4,729,377 | A | 3/1988 | Granek et al. |
| 4,763,660 | A | 8/1988 | Kroll et al. |
| 4,781,200 | A | 11/1988 | Baker |
| 4,785,822 | A | 11/1988 | Wallace |
| 4,815,964 | A | 3/1989 | Cohen et al. |
| 4,842,557 | A | 6/1989 | Muz |
| 4,850,356 | A | 7/1989 | Heath |
| 4,909,260 | A | 3/1990 | Salem et al. |
| 4,947,846 | A | 8/1990 | Kitagawn et al. |
| 4,957,109 | A | 9/1990 | Groeger et al. |
| 4,974,594 | A | 12/1990 | Berlin |
| 5,080,604 | A | 1/1992 | Rider et al. |
| 5,083,238 | A | 1/1992 | Bousman |
| 5,083,933 | A | 1/1992 | Colleran et al. |
| 5,104,253 | A | 4/1992 | Zielinski et al. |
| 5,104,334 | A | 4/1992 | Honma et al. |
| 5,131,854 | A | 7/1992 | Jose et al. |
| 5,137,466 | A | 8/1992 | Endo et al. |
| 5,154,646 | A | 10/1992 | Shoup |
| 5,158,469 | A | 10/1992 | Martin |
| 5,160,276 | A | 11/1992 | Marsh et al. |
| 5,173,059 | A | 12/1992 | Sato et al. |
| 5,176,343 | A | 1/1993 | Cheney et al. |
| 5,178,556 | A | 1/1993 | Chen |
| 5,180,312 | A | 1/1993 | Martin |
| 5,190,467 | A | 3/1993 | Ohta |
| 5,192,226 | A | 3/1993 | Wang |
| 5,197,901 | A | 3/1993 | Hashiguchi |
| 5,199,897 | A | 4/1993 | Hashiguchi |
| 5,201,669 | A | 4/1993 | Lin |
| 5,203,715 | A | 4/1993 | Yamamoto |
| 5,203,719 | A | 4/1993 | Kozono |
| 5,207,594 | A | 5/1993 | Olson |
| 5,224,479 | A | 7/1993 | Sekine |
| 5,232,383 | A | 8/1993 | Barnick |
| 5,234,357 | A | 8/1993 | Yamaguchi |
| 5,243,510 | A | 9/1993 | Cheney |
| 5,263,481 | A | 11/1993 | Axelgaard |
| 5,276,443 | A | 1/1994 | Gates et al. |
| 5,278,759 | A | 1/1994 | Berra et al. |
| 5,279,308 | A | 1/1994 | DiSabito et al. |
| 5,293,013 | A | 3/1994 | Takahashi |
| 5,320,621 | A | 6/1994 | Gordon et al. |
| 5,326,272 | A | 7/1994 | Harhen et al. |
| 5,332,330 | A | 7/1994 | Kaneko |
| 5,338,219 | A | 8/1994 | Hiramoto |
| 5,341,806 | A | 8/1994 | Gadsby et al. |
| 5,341,812 | A | 8/1994 | Allaire et al. |
| 5,353,793 | A | 10/1994 | Bornn |
| 5,354,216 | A | 10/1994 | Cruise et al. |
| 5,362,249 | A | 11/1994 | Carter |
| 5,370,116 | A | 12/1994 | Rollman et al. |
| 5,370,550 | A | 12/1994 | Alwine et al. |
| 5,376,016 | A | 12/1994 | Inaba et al. |
| 5,378,168 | A | 1/1995 | Sumida |
| 5,380,223 | A | 1/1995 | Marsh et al. |
| 5,382,176 | A | 1/1995 | Norden |
| 5,383,794 | A | 1/1995 | Davis et al. |
| 5,387,116 | A | 2/1995 | Wang |
| 5,387,127 | A | 2/1995 | Wang |
| 5,399,045 | A | 3/1995 | Yoneda et al. |
| 5,405,269 | A | 4/1995 | Stupecky |
| 5,415,164 | A | 5/1995 | Faupel et al. |
| 5,429,526 | A | 7/1995 | Ann |
| 5,431,166 | A | 7/1995 | Macur |
| 5,454,739 | A | 10/1995 | Strand |
| 5,462,448 | A | 10/1995 | Kida et al. |
| 5,484,739 | A | 1/1996 | Lee et al. |
| 5,486,117 | A | 1/1996 | Chang |
| 5,507,290 | A | 4/1996 | Kelly et al. |
| 5,507,665 | A | 4/1996 | Oda |
| 5,507,668 | A | 4/1996 | Lambrinos et al. |
| 5,509,822 | A | 4/1996 | Negus et al. |
| 5,511,553 | A | 4/1996 | Segalowitz |
| 5,546,950 | A | 8/1996 | Schoeckert et al. |
| 5,558,535 | A | 9/1996 | Saka et al. |
| 5,564,939 | A | 10/1996 | Maitani et al. |
| 5,582,180 | A | 12/1996 | Manset et al. |
| 5,584,719 | A | 12/1996 | Tsuji et al. |
| D377,219 | S | 1/1997 | Strand et al. |
| 5,599,199 | A | 2/1997 | Wright |
| 5,603,632 | A | 2/1997 | Johannes et al. |
| 5,611,708 | A | 3/1997 | Mizunuma et al. |
| 5,613,870 | A | 3/1997 | Traver, Jr. |
| 5,615,674 | A | 4/1997 | Maurer |
| 5,622,168 | A | 4/1997 | Keusch et al. |
| 5,624,271 | A | 4/1997 | Childs et al. |
| 5,624,281 | A | 4/1997 | Christensson |
| 5,626,135 | A | 5/1997 | Sanfilippo |
| 5,632,274 | A | 5/1997 | Quedens et al. |
| 5,651,689 | A | 7/1997 | Plyler et al. |
| 5,653,606 | A | 8/1997 | Chrysostomou |
| 5,674,088 | A | 10/1997 | Roche et al. |
| 5,676,694 | A | 10/1997 | Boser et al. |
| 5,679,022 | A | 10/1997 | Cappa |
| 5,679,029 | A | 10/1997 | Saunier et al. |
| 5,685,303 | A | 11/1997 | Rollman et al. |
| 5,695,355 | A | 12/1997 | Hasenfratz et al. |
| 5,702,265 | A | 12/1997 | Yamaguchi |
| 5,704,351 | A | 1/1998 | Mortara et al. |
| 5,711,684 | A | 1/1998 | Inoue et al. |
| 5,718,596 | A | 2/1998 | Inaba et al. |
| 5,724,025 | A | 3/1998 | Tavori |

(56) References Cited

U.S. PATENT DOCUMENTS

| | | |
|---|---|---|
| 5,724,984 A | 3/1998 | Arnold et al. |
| 5,725,525 A | 3/1998 | Kordis |
| 5,741,155 A | 4/1998 | Herman |
| 5,749,746 A | 5/1998 | Tan et al. |
| 5,769,650 A | 6/1998 | Aoyama et al. |
| 5,772,591 A | 6/1998 | Cram |
| 5,775,953 A | 7/1998 | Yamanashi et al. |
| 5,782,647 A | 7/1998 | Okura et al. |
| 5,782,761 A | 7/1998 | Gusakov |
| 5,782,892 A | 7/1998 | Castle et al. |
| 5,788,527 A | 8/1998 | Sanders et al. |
| 5,791,918 A | 8/1998 | Pierce |
| 5,797,854 A | 8/1998 | Hedgecock |
| 5,806,152 A | 9/1998 | Saitou et al. |
| 5,813,404 A | 9/1998 | Devlin et al. |
| 5,813,979 A | 9/1998 | Wolfer |
| 5,827,086 A | 10/1998 | Fukuda |
| 5,830,000 A | 11/1998 | Shifflett et al. |
| 5,836,783 A | 11/1998 | Morisawa et al. |
| 5,843,141 A | 12/1998 | Bischoff et al. |
| 5,848,456 A | 12/1998 | Sjoqvist |
| 5,865,740 A | 2/1999 | Kelly et al. |
| 5,865,741 A | 2/1999 | Kelly et al. |
| 5,871,451 A | 2/1999 | Unger et al. |
| 5,873,747 A | 2/1999 | Tsuji |
| 5,876,232 A | 3/1999 | Matsushita et al. |
| 5,895,284 A | 4/1999 | Kocher et al. |
| 5,895,298 A | 4/1999 | Faupel |
| 5,904,579 A | 5/1999 | McLean et al. |
| 5,913,834 A | 6/1999 | Francais |
| 5,916,159 A | 6/1999 | Kelly et al. |
| 5,931,689 A | 8/1999 | Patel |
| 5,931,861 A | 8/1999 | Werner et al. |
| 5,934,926 A | 8/1999 | Gabrisko, Jr. et al. |
| 5,937,950 A | 8/1999 | Adams et al. |
| 5,938,470 A | 8/1999 | Kashiyama |
| 5,938,597 A | 8/1999 | Starbucker |
| 5,941,725 A | 8/1999 | Brennan et al. |
| 5,944,562 A | 8/1999 | Christensson |
| 5,951,316 A | 9/1999 | Kawano et al. |
| 5,964,624 A | 10/1999 | Pernelle |
| 5,968,087 A | 10/1999 | Hess et al. |
| 5,971,790 A | 10/1999 | Rohde |
| 5,971,799 A | 10/1999 | Swade |
| 5,980,332 A | 11/1999 | Tsuji et al. |
| 5,984,717 A | 11/1999 | Lee |
| 5,997,334 A | 12/1999 | Goto |
| 6,006,125 A | 12/1999 | Kelly et al. |
| 6,027,359 A | 2/2000 | Aoki et al. |
| 6,032,063 A | 2/2000 | Hoar et al. |
| 6,032,064 A | 2/2000 | Devlin et al. |
| 6,038,479 A | 3/2000 | Werner et al. |
| 6,038,481 A | 3/2000 | Werner et al. |
| 6,050,838 A | 4/2000 | Norizuki et al. |
| 6,055,448 A | 4/2000 | Anderson et al. |
| 6,062,902 A | 5/2000 | Buckles et al. |
| 6,066,093 A | 5/2000 | Kelly et al. |
| 6,074,234 A | 6/2000 | Hasegawa |
| 6,098,127 A | 8/2000 | Kwang |
| 6,109,948 A | 8/2000 | Kuo |
| 6,115,623 A | 9/2000 | McFee |
| 6,116,940 A | 9/2000 | Bertens et al. |
| 6,122,536 A | 9/2000 | Sun et al. |
| 6,122,544 A | 9/2000 | Organ |
| 6,129,666 A | 10/2000 | DeLuca et al. |
| 6,132,233 A | 10/2000 | Fukuda |
| 6,139,350 A | 10/2000 | Mathesius |
| 6,139,360 A | 10/2000 | Hayashi |
| 6,152,778 A | 11/2000 | Dalton |
| 6,155,864 A | 12/2000 | Yoshiura |
| 6,157,851 A | 12/2000 | Kelly et al. |
| 6,165,017 A | 12/2000 | Kuo |
| 6,168,453 B1 | 1/2001 | Kuo |
| 6,171,139 B1 | 1/2001 | Sato et al. |
| 6,190,385 B1 | 2/2001 | Tom et al. |
| 6,203,354 B1 | 3/2001 | Kuwahara |
| 6,219,568 B1 | 4/2001 | Kelly et al. |
| 6,219,569 B1 | 4/2001 | Kelly et al. |
| 6,223,088 B1 | 4/2001 | Scharnberg et al. |
| 6,232,366 B1 | 5/2001 | Wang et al. |
| 6,234,827 B1 | 5/2001 | Nishio et al. |
| 6,236,874 B1 | 5/2001 | Devlin et al. |
| 6,240,323 B1 | 5/2001 | Calenzo, Sr. et al. |
| 6,247,963 B1 | 6/2001 | Rattner |
| 6,250,955 B1 | 6/2001 | Archuleta |
| 6,254,425 B1 | 7/2001 | Shchervinsky |
| 6,257,914 B1 | 7/2001 | Comerci et al. |
| 6,257,925 B1 | 7/2001 | Jones |
| 6,280,209 B1 | 8/2001 | Bassler et al. |
| 6,280,227 B1 | 8/2001 | Terada et al. |
| 6,280,243 B1 | 8/2001 | Liu et al. |
| 6,283,789 B1 | 9/2001 | Tsai |
| 6,290,530 B1 | 9/2001 | Chang |
| 6,298,255 B1 | 10/2001 | Cordero et al. |
| 6,304,783 B1 | 10/2001 | Lyster et al. |
| 6,312,297 B1 | 11/2001 | Lorkowski |
| 6,324,432 B1 | 11/2001 | Rigaux et al. |
| D452,318 S | 12/2001 | Merry et al. |
| 6,339,720 B1 | 1/2002 | Anzellini et al. |
| 6,340,306 B1 | 1/2002 | Daoud |
| 6,356,779 B1 | 3/2002 | Katzenmaier et al. |
| 6,358,083 B1 | 3/2002 | Kraft |
| 6,360,119 B1 | 3/2002 | Roberts |
| 6,364,685 B1 | 4/2002 | Manning |
| 6,383,010 B1 | 5/2002 | Mayo et al. |
| 6,383,011 B2 | 5/2002 | Chen |
| 6,383,036 B1 | 5/2002 | Steinhauser et al. |
| 6,386,917 B1 | 5/2002 | Sakaguchi |
| 6,393,317 B1 | 5/2002 | Fukuda |
| 6,394,953 B1 | 5/2002 | Devlin et al. |
| 6,398,575 B1 | 6/2002 | Bresson |
| 6,398,577 B1 | 6/2002 | Simmel et al. |
| 6,400,977 B1 | 6/2002 | Kelly et al. |
| 6,411,834 B1 | 6/2002 | Nagai |
| 6,413,112 B2 | 7/2002 | Semmeling et al. |
| 6,415,169 B1 | 7/2002 | Kornrumpf et al. |
| 6,419,636 B1 | 7/2002 | Young et al. |
| 6,434,410 B1 | 8/2002 | Cordero et al. |
| 6,447,170 B1 | 9/2002 | Takahashi et al. |
| 6,453,186 B1 | 9/2002 | Lovejoy et al. |
| 6,454,577 B1 | 9/2002 | Yi |
| 6,454,590 B1 | 9/2002 | Goodrich et al. |
| 6,454,605 B1 | 9/2002 | Bassler et al. |
| 6,456,872 B1 | 9/2002 | Faisander |
| 6,461,179 B1 | 10/2002 | Sullivan et al. |
| 6,487,430 B1 | 11/2002 | Henderson et al. |
| 6,494,744 B1 | 12/2002 | Lee |
| 6,514,099 B2 | 2/2003 | Endo |
| 6,517,372 B1 | 2/2003 | Jones |
| 6,531,657 B1 | 3/2003 | Jones, Jr. et al. |
| 6,533,600 B1 | 3/2003 | Kashiyama et al. |
| 6,540,549 B2 | 4/2003 | Rupert |
| 6,551,117 B2 | 4/2003 | Poplawski et al. |
| 6,553,246 B1 | 4/2003 | Wenger |
| 6,553,250 B2 | 4/2003 | Rantala |
| 6,558,189 B2 | 5/2003 | Groebe et al. |
| 6,561,834 B2 | 5/2003 | Chen |
| 6,564,079 B1 | 5/2003 | Cory et al. |
| 6,565,388 B1 | 5/2003 | Van Woensel et al. |
| 6,567,680 B2 | 5/2003 | Swetlik et al. |
| 6,575,759 B1 | 6/2003 | Ollivier |
| 6,575,794 B1 | 6/2003 | Nakamura |
| 6,582,252 B1 | 6/2003 | Lin |
| 6,589,066 B1 | 7/2003 | Wu |
| 6,592,391 B1 | 7/2003 | Wu |
| 6,592,404 B2 | 7/2003 | Endo |
| 6,604,963 B1 | 8/2003 | Lin |
| 6,607,397 B1 | 8/2003 | Zhang et al. |
| 6,609,018 B2 | 8/2003 | Cory et al. |
| 6,609,833 B1 | 8/2003 | Miyachi et al. |
| 6,611,705 B2 | 8/2003 | Hopman et al. |
| 6,612,860 B2 | 9/2003 | Droesbeke |
| 6,619,976 B2 | 9/2003 | Huetter et al. |
| 6,619,989 B1 | 9/2003 | Yi |

(56) References Cited

U.S. PATENT DOCUMENTS

| | | |
|---|---|---|
| 6,623,312 B2 | 9/2003 | Merry et al. |
| 6,636,754 B1 | 10/2003 | Baura et al. |
| 6,647,286 B1 | 11/2003 | Kato et al. |
| 6,648,665 B1 | 11/2003 | Wu |
| 6,648,666 B1 | 11/2003 | Wu |
| 6,654,626 B2 | 11/2003 | Devlin et al. |
| 6,655,979 B1 | 12/2003 | Lee |
| 6,659,790 B1 | 12/2003 | Wi |
| 6,663,412 B2 | 12/2003 | Aramoto et al. |
| 6,663,419 B2 | 12/2003 | Vaden |
| 6,663,420 B1 | 12/2003 | Xiao |
| 6,663,570 B2 | 12/2003 | Mott et al. |
| 6,669,510 B2 | 12/2003 | Yamawaki et al. |
| 6,688,894 B2 | 2/2004 | Knox, Jr. et al. |
| 6,688,907 B2 | 2/2004 | Yamaoka et al. |
| 6,702,602 B2 | 3/2004 | Wu |
| 6,702,603 B2 | 3/2004 | Wu |
| 6,702,616 B1 | 3/2004 | Chang et al. |
| 6,709,284 B1 | 3/2004 | Avlonitis |
| 6,716,165 B1 | 4/2004 | Flanders et al. |
| 6,722,912 B2 | 4/2004 | Wu |
| 6,736,650 B1 | 5/2004 | Chen |
| 6,743,053 B2 | 6/2004 | Wu |
| 6,748,797 B2 | 6/2004 | Breed et al. |
| 6,751,493 B2 | 6/2004 | Wenger |
| 6,755,689 B2 | 6/2004 | Zhang et al. |
| 6,768,921 B2 | 7/2004 | Organ et al. |
| 6,773,293 B1 | 8/2004 | Lee |
| 6,780,065 B2 | 8/2004 | Schwarz |
| 6,786,755 B2 | 9/2004 | Dambach et al. |
| 6,786,764 B2 | 9/2004 | Sivertsen |
| 6,816,744 B2 | 11/2004 | Garfield et al. |
| 6,832,928 B2 | 12/2004 | Suzuki et al. |
| 6,837,734 B2 | 1/2005 | Ushio et al. |
| 6,847,836 B1 | 1/2005 | Sujdak |
| 6,848,926 B2 | 2/2005 | Ling et al. |
| 6,851,969 B2 | 2/2005 | Archuletta |
| 6,860,750 B1 | 3/2005 | Wu |
| 6,866,535 B2 | 3/2005 | Uchida |
| 6,881,098 B2 | 4/2005 | Jeansonne et al. |
| 6,891,379 B2 | 5/2005 | Kelly et al. |
| 6,913,482 B1 | 7/2005 | Wu |
| 6,939,158 B2 | 9/2005 | Moffett et al. |
| 6,939,345 B2 | 9/2005 | Knight et al. |
| 6,945,796 B2 | 9/2005 | Bassler et al. |
| 6,945,807 B1 | 9/2005 | Wu |
| 6,948,973 B1 | 9/2005 | Hsu et al. |
| 6,970,731 B1 | 11/2005 | Jayaraman et al. |
| 6,973,341 B2 | 12/2005 | Watson |
| 6,973,343 B2 | 12/2005 | Wenger |
| 6,980,852 B2 | 12/2005 | Jersey-Willuhn et al. |
| 6,984,143 B2 | 1/2006 | Roese |
| 6,997,733 B2 | 2/2006 | Peng |
| 7,004,787 B2 | 2/2006 | Milan |
| 7,008,255 B1 | 3/2006 | Wang |
| 7,025,618 B2 | 4/2006 | Fukuda |
| 7,025,628 B2 | 4/2006 | LaMeres et al. |
| 7,029,286 B2 | 4/2006 | Hall et al. |
| 7,033,207 B2 | 4/2006 | Nimura |
| 7,041,918 B1 | 5/2006 | Wu |
| 7,056,134 B2 | 6/2006 | Martin et al. |
| 7,056,141 B2 | 6/2006 | Moffett et al. |
| 7,077,711 B1 | 7/2006 | Moore |
| 7,081,008 B2 | 7/2006 | Tan |
| 7,081,026 B2 | 7/2006 | Schwarz |
| 7,083,480 B2 | 8/2006 | Silber |
| 7,085,598 B2 | 8/2006 | Sato |
| 7,104,801 B1 | 9/2006 | Brodnick et al. |
| 7,110,804 B2 | 9/2006 | Baumer et al. |
| 7,117,590 B2 | 10/2006 | Koenig et al. |
| 7,118,411 B2 | 10/2006 | Huang et al. |
| 7,127,279 B2 | 10/2006 | Finneran et al. |
| 7,128,600 B2 | 10/2006 | Osypka |
| 7,134,908 B2 | 11/2006 | Wu |
| 7,137,839 B2 | 11/2006 | Dilliner et al. |
| 7,144,268 B2 | 12/2006 | Koenig et al. |
| 7,150,655 B2 | 12/2006 | Mastrototaro et al. |
| D535,029 S | 1/2007 | McAtamney et al. |
| 7,160,136 B2 | 1/2007 | Zhang et al. |
| 7,169,107 B2 | 1/2007 | Jersey-Willuhn et al. |
| 7,179,111 B2 | 2/2007 | Van Der Mee et al. |
| 7,179,113 B2 | 2/2007 | Koenig et al. |
| 7,182,630 B1 | 2/2007 | Su |
| 7,184,820 B2 | 2/2007 | Jersey-Willuhn et al. |
| 7,189,097 B2 | 3/2007 | Benham |
| 7,197,357 B2 | 3/2007 | Istvan et al. |
| 7,198,502 B2 | 4/2007 | Koenig et al. |
| 7,201,599 B2 | 4/2007 | Holub |
| 7,207,825 B2 | 4/2007 | Le Gallic et al. |
| 7,214,107 B2 | 5/2007 | Powell et al. |
| 7,236,825 B2 | 6/2007 | Wang |
| 7,252,542 B2 | 8/2007 | Chen |
| 7,252,556 B2 | 8/2007 | Anbo et al. |
| 7,252,565 B2 | 8/2007 | Hunter |
| 7,255,609 B1 | 8/2007 | Epstein |
| 7,258,566 B2 | 8/2007 | Koenig et al. |
| 7,264,510 B2 | 9/2007 | Koenig et al. |
| 7,270,568 B2 | 9/2007 | Osypka |
| 7,270,580 B2 | 9/2007 | Bradley et al. |
| 7,272,427 B2 | 9/2007 | Ristolainen |
| 7,272,428 B2 | 9/2007 | Hopman et al. |
| 7,275,951 B2 | 10/2007 | Shigeta et al. |
| 7,281,937 B2 | 10/2007 | Reed et al. |
| 7,287,998 B2 | 10/2007 | Masai |
| 7,303,430 B2 | 12/2007 | Butcher |
| 7,318,740 B1 | 1/2008 | Henry et al. |
| 7,319,895 B2 | 1/2008 | Klefstad-Sillinville et al. |
| 7,322,849 B2 | 1/2008 | Sutton |
| 7,329,139 B2 | 2/2008 | Benham |
| 7,333,850 B2 | 2/2008 | Marossero et al. |
| 7,347,710 B2 | 3/2008 | Ohtaka et al. |
| 7,347,826 B1 | 3/2008 | Karicherla et al. |
| 7,359,751 B1 | 4/2008 | Erickson et al. |
| 7,361,058 B1 | 4/2008 | Lien et al. |
| 7,364,440 B2 | 4/2008 | Gobron et al. |
| 7,371,102 B2 | 5/2008 | Sakamoto et al. |
| 7,373,196 B2 | 5/2008 | Ryu et al. |
| 7,374,448 B1 | 5/2008 | Jepsen et al. |
| 7,381,082 B2 | 6/2008 | Lai |
| 7,390,224 B2 | 6/2008 | Sodemann et al. |
| 7,396,246 B2 | 7/2008 | Okada et al. |
| 7,399,195 B2 | 7/2008 | Kim et al. |
| 7,401,946 B2 | 7/2008 | Laukhuf |
| 7,402,071 B2 | 7/2008 | Ohtaka et al. |
| 7,413,461 B2 | 8/2008 | Dawiedczyk et al. |
| 7,413,485 B2 | 8/2008 | Lappoehn |
| 7,416,440 B2 | 8/2008 | Homyk et al. |
| 7,422,437 B1 | 9/2008 | Lin et al. |
| 7,422,452 B2 | 9/2008 | Achter et al. |
| 7,445,512 B1 | 11/2008 | Lai |
| 7,445,522 B2 | 11/2008 | Burns |
| 7,462,074 B1 | 12/2008 | Devlin et al. |
| 7,473,141 B2 | 1/2009 | Liao |
| 7,488,187 B2 | 2/2009 | Wolf |
| 7,494,383 B2 | 2/2009 | Cohen et al. |
| 7,497,738 B2 | 3/2009 | Kuo |
| 7,503,807 B2 | 3/2009 | Martin et al. |
| 7,556,535 B2 | 7/2009 | Liao |
| 7,581,992 B1 | 9/2009 | Liu et al. |
| 7,585,182 B2 | 9/2009 | Asante et al. |
| 7,591,673 B2 | 9/2009 | Chan et al. |
| 7,604,511 B1 | 10/2009 | Johnson |
| 7,618,377 B2 | 11/2009 | McAtamney et al. |
| 7,632,130 B2 | 12/2009 | Sami |
| 7,666,028 B2 | 2/2010 | Meleck |
| D629,358 S | 12/2010 | Slippy et al. |
| 8,038,484 B2 * | 10/2011 | Selvitelli et al. ............... 439/729 |
| 8,152,571 B2 * | 4/2012 | Selvitelli et al. ............... 439/729 |
| 8,255,041 B2 | 8/2012 | Istvan et al. |
| 8,408,507 B2 | 4/2013 | Liu |
| 8,408,948 B2 | 4/2013 | Selvitelli et al. |
| 8,414,315 B2 | 4/2013 | Dekoski |
| 8,690,611 B2 * | 4/2014 | Selvitelli et al. ............... 439/729 |
| 8,694,080 B2 | 4/2014 | Farrior |

(56) References Cited

U.S. PATENT DOCUMENTS

| | | | |
|---|---|---|---|
| 8,795,004 B2* | 8/2014 | Selvitelli et al. ............ 439/729 | |
| 2001/0053639 A1 | 12/2001 | Endo | |
| 2002/0133069 A1 | 9/2002 | Roberts | |
| 2002/0138011 A1 | 9/2002 | Rantala | |
| 2002/0188216 A1 | 12/2002 | Kayyali et al. | |
| 2003/0068914 A1 | 4/2003 | Merry et al. | |
| 2003/0068918 A1 | 4/2003 | Christensson | |
| 2004/0073127 A1 | 4/2004 | Istvan et al. | |
| 2004/0127802 A1 | 7/2004 | Istvan et al. | |
| 2004/0176674 A1 | 9/2004 | Nazeri | |
| 2004/0203273 A1 | 10/2004 | Schwarz | |
| 2005/0164551 A1 | 7/2005 | Wlos | |
| 2005/0177052 A1 | 8/2005 | Istvan et al. | |
| 2005/0203349 A1 | 9/2005 | Nanikashvill | |
| 2006/0004273 A1 | 1/2006 | Lobodzinski | |
| 2006/0073728 A1 | 4/2006 | Zaiken et al. | |
| 2006/0286861 A1 | 12/2006 | Avevor et al. | |
| 2007/0038057 A1 | 2/2007 | Nam et al. | |
| 2007/0260133 A1 | 11/2007 | Meyer | |
| 2008/0132106 A1 | 6/2008 | Burnes et al. | |
| 2008/0132773 A1 | 6/2008 | Burnes et al. | |
| 2008/0177168 A1 | 7/2008 | Callahan et al. | |
| 2009/0099423 A1 | 4/2009 | Al-Ali et al. | |
| 2009/0149731 A1 | 6/2009 | Selvitelli et al. | |
| 2009/0221153 A1 | 9/2009 | Santangelo et al. | |
| 2011/0092833 A1 | 4/2011 | Farrior | |
| 2011/0275252 A1 | 11/2011 | Selvitelli et al. | |
| 2012/0196474 A1 | 8/2012 | Selvitelli et al. | |
| 2013/0023750 A1 | 1/2013 | Callahan et al. | |
| 2013/0189881 A1 | 7/2013 | Selvitelli et al. | |
| 2014/0170896 A1 | 6/2014 | Selvitelli et al. | |
| 2014/0180148 A1 | 6/2014 | Coggins et al. | |

FOREIGN PATENT DOCUMENTS

| | | |
|---|---|---|
| DE | 9002539 U1 | 5/1990 |
| DE | 10225621 | 1/2004 |
| DE | 102004032410 | 1/2006 |
| EP | 0 766 946 A2 | 4/1997 |
| EP | 0 799 628 | 10/1997 |
| EP | 1 050 269 | 11/2000 |
| EP | 1645224 | 4/2008 |
| EP | 1 932 470 | 6/2008 |
| EP | 2 070 474 | 6/2009 |
| GB | 162804 | 5/1921 |
| JP | 10248820 A | 9/1998 |
| JP | 2003/010138 | 1/2003 |
| JP | 2004/282608 | 10/2004 |
| WO | WO 03 047427 | 6/2003 |
| WO | WO 2008/092098 A2 | 7/2008 |
| WO | WO 2013/013370 A1 | 1/2013 |

OTHER PUBLICATIONS

U.S. Appl. No. 13/987,326.
Simpson U.S. Appl. No. 14/209,278, filed Mar. 13, 2014 30 pages.
A&D Company, Limited, "Vital Sensor Graphic Model", No. TM-2560G/TM2564G-TM-2564GP/TM2564GP, Jan. 1, 2004; pp. 1-62.
Andreas Boos et al.; "A New Lightweight Fetal Telemetry System", Dec. 1995; Hewlett-Packard Journal; 12 pages.
Tyco Healthcare Kendal, ECG Electrodes Where Quality leads 2003 8 pages.
European Search Report Corresponding to European Application No. EP 07 25 3850, Date of completion is Dec. 21, 2007 3 pages.
EP Notice Under Rule 161 dated Feb. 28, 2014, for EP App. No. 11869957.8 3 pages.
Response to Written Opinion and Claims Filed on Jun. 11, 2014, for EP App. No. 11869957.8 6 pages.
Search Report and Written Opinion dated Apr. 12, 2012, for App. No. PCT/CN2011/077506 14 pages.
First Office Action dated Jul. 26, 2011, for Chinese App. No. 200810191090.1 6 pages.
Letter regarding Response to Office Action dated Nov. 22, 2011, for Chinese App. No. 200810191090.1 9 pages.
Response to Office Action dated Dec. 12, 2011, for Chinese App. No. 200810191090.1 18 pages.
Letter dated May 11, 2012 enclosing Second Office Action dated Apr. 27, 2012, for Chinese App. No. 200810191090.1 6 pages.
Notification of Response to Second Office Action dated Jun. 11, 2012, for Chinese App. No. 200810191090.1 5 pages.
Letter dated Dec. 20, 2012 enclosing Grant Notification dated Dec. 19, 2012, for Chinese App. No. 200810191090.1 4 pages.
Divisional Application as filed on Mar. 1, 2013, for Chinese App. No. 200810191090.1 37 pages.
European Office Action dated Nov. 19, 2010, for EP App. No. 08171185.5 1 page.
Letter dated Dec. 22, 2010 in response to EP Office Action Nov. 19, 2010 European Office Action for EP App. No. 08171185.5 1 page.
Response to Office Action dated Oct. 3, 2012 for EP App. No. 08171185.5 2 page.
Letter dated Oct. 4, 2012 and copy of Divisional for EP App. No. 08171185.5 39 pages.
Letter dated Dec. 16, 2013 in response to Communication dated Jun. 24, 2013, for EP App. No. 08171185.5 4 pages.
Examination Report dated Jun. 24, 2013, for EP App. No. 08171185.5 4 pages.
Extended Search Report dated Mar. 7, 2012, for EP App. No. 08171185.5 8 pages.
Letter dated Apr. 2, 2012 and Office Action for Mexican App. No. MX/a/2008/015927 3 pages.
Letter dated May 15, 2012 and Response to Office Action for Mexican App. No. MX/a/2008/015927 Filed on Dec. 11, 2008 9 Pages.
Letter dated Jun. 26, 2012 and Regarding Notice of Allowance with allowed claims for Mexican App. No. MX/a/2008/015927 Filed on Dec. 11, 2008 7 Pages.
Letter dated Feb. 5, 2014 Confirming receipt of Notice of Allowance, for Mexican App. No. MX/a/2012/009542 2 pages.
Letter dated Feb. 25, 2013 also enclosing Office Action for App. No. MX/a/2012/009542 3 pages.
Letter and Response to Office Action dated Apr. 23, 2013, for Mexican App. No. MX/a/2012/009542 20 pages.
Letter dated Sep. 18, 2013 and Office Action for Mexican App. No. MX/a/2012/009542 4 pages.
Letter dated Oct. 30, 2013 and Response to Office Action for Mexican App. No. MX/a/2012/009542 5 pages.
Letter dated Jun. 10, 2014 Confirming receipt of Notice of Allowance for Mexican App. No. MX/a/2013/012636 2 pages.
Letter dated Jun. 10, 2014 Confirming receipt of Notice of Allowance for Mexican App. No. MX/a/2013/012635 2 pages.
Extended Search Report dated Oct. 8, 2013, for EP App. No. 12187209.7009542 6 pages.
European Notice Responding to Search Report dated Nov. 11, 2013, for EP App. No. 12187209.7009542 2 pages.
European Exam Report dated Mar. 11, 2014, for EP App. No. 12187209.7009542 4 pages.
Response dated Jan. 27, 2014 to Extended Search Report dated Oct. 8, 2013, for EP App. No. 12187209.7009542 16 pages.
Response to Exam Report dated Jun. 24, 2014 for EP App. No. 12187209.7009542 8 pages.
Response dated Nov. 2, 2011 to Communication dated May 10, 2011 for EP App. No. 10013624.10 5 pages.
Extended Search Report dated Apr. 4, 2011, for EP App. No. 10013624.10 14 pages.
European Exam Report dated Nov. 12, 2013, for EP App. No. 12187209.7009542 6 pages.
Response to Communication dated Mar. 17, 2014 for EP App. No. 12187209.7009542 14 pages.
European Office Action dated May 21, 2014, for EP App. No. 12187209.7009542 5 pages.
European Search Report dated May 23, 2014, for EP App. No. 14162076.5 10 pages.
Response to Chinese Office Action dated May 4, 2011, for Chinese App. No. 201010624971.50 21 pages.
Notification of Entry into Examination Procedure dated Oct. 11, 2012, for Chinese App. No. 201010624971.50 2 Pages.

(56) References Cited

OTHER PUBLICATIONS

Receipt of First Office Action dated Nov. 28, 2013, for Chinese App. No. 201010624971.50 136 Pages.
Response to Office Action dated Apr. 14, 2014, for Chinese App. No. 201010624971.50 34 Pages.
Search Report dated Jun. 4, 2014, for App. No. PCT/US2014/019479 10 pages.
Article 19 Amendment as filed dated Jul. 2, 2014 for App. No. PCT/US2014/019479 10 pages.
Letter and Chinese Office Action dated Jul. 1, 2014, for Chinese App. No. 2013100649128.3 38 pages.
Voluntary Amendment with English claims dated Jul. 15, 2014 for Application No. 201180072455.9 7 pages.
Callahan U.S. Appl. No. 13/987,326, filed Mar. 15, 2013 37 pages.
Simpson U.S. Appl. No. 14/209,278, filed Mar. 13, 2014 21 pages.
Zhou U.S. Appl. No. 14/160,798, filed Jan. 22, 2014 26 pages.
U.S. Appl. No. 12/330,550.
U.S. Appl. No. 13/182,656.
U.S. Appl. No. 13/443,096.
U.S. Appl. No. 13/785,713, filed Mar. 5, 2013, 200pages, Part 1.
U.S. Appl. No. 13/785,713, filed Mar. 5, 2013, 200 pages, Part 2.
U.S. Appl. No. 13/785,713, filed Mar. 5, 2013, 200 pages, Part 3.
U.S. Appl. No. 13/785,713, filed Mar. 5, 2013, 200 pages, Part 4.
U.S. Appl. No. 13/785,713, filed Mar. 5, 2013, 200 pages, Part 5.
U.S. Appl. No. 13/785,713, filed Mar. 5, 2013, 200 pages, Part 6.
U.S. Appl. No. 13/785,713, filed Mar. 5, 2013, 200 pages, Part 7.
U.S. Appl. No. 13/785,713, filed Mar. 5, 2013, 200 pages, Part 8.
U.S. Appl. No. 13/785,713, filed Mar. 5, 2013, 200 pages, Part 9.
U.S. Appl. No. 13/785,713, filed Mar. 5, 2013, 200 pages, Part 10.
U.S. Appl. No. 13/785,713, filed Mar. 5, 2013, 200 pages, Part 11.
U.S. Appl. No. 13/785,713, filed Mar. 5, 2013, 200 pages, Part 12.
U.S. Appl. No. 13/785,713, filed Mar. 5, 2013, 200 pages, Part 13.
U.S. Appl. No. 13/785,713, filed Mar. 5, 2013, 18 pages, Part 14.
U.S. Appl. No. 14/041,471; Part 1 of 16; 350 Pages.
U.S. Appl. No. 14/041,471; Part 2 of 16; 350 Pages.
U.S. Appl. No. 14/041,471; Part 3 of 16; 350 Pages.
U.S. Appl. No. 14/041,471; Part 4 of 16; 350 Pages.
U.S. Appl. No. 14/041,471; Part 5 of 16; 350 Pages.
U.S. Appl. No. 14/041,471; Part 6 of 16; 350 Pages.
U.S. Appl. No. 14/041,471; Part 7 of 16; 350 Pages.
U.S. Appl. No. 14/041,471; Part 8 of 16; 350 Pages.
U.S. Appl. No. 14/041,471; Part 9 of 16; 200 Pages.
U.S. Appl. No. 14/041,471; Part 9A of 16; 150 Pages.
U.S. Appl. No. 14/041,471; Part 10 of 16; 350 Pages.
U.S. Appl. No. 14/041,471; Part 11 of 16; 350 Pages.
U.S. Appl. No. 14/041,471; Part 12 of 16; 350 Pages.
U.S. Appl. No. 14/041,471; Part 13 of 16; 350 Pages.
U.S. Appl. No. 14/041,471; Part 14 of 16; 350 Pages.
U.S. Appl. No. 14/041,471; Part 15 of 16; 350 Pages.
U.S. Appl. No. 14/041,471; Part 16 of 16; 129 Pages.
U.S. Appl. No. 12/876,316; Part 1 of 5; 250 Pages.
U.S. Appl. No. 12/876,316; Part 2 of 5; 250 Pages.
U.S. Appl. No. 12/876,316; Part 3 of 5; 250 Pages.
U.S. Appl. No. 12/876,316; Part 4 of 5; 250 Pages.
U.S. Appl. No. 12/876,316; Part 5 of 5; 238 Pages.
U.S. Appl. No. 14/195,140; 314 Pages.
Chinese Office Action dated Jan. 12, 2015; with English Translation for Chinese App. No. 200180072455.9; 15 pages.
International Search Report and Written Opinion dated Sep. 9, 2014 for PCT Application No. PCT/US2014/027328; 16 pages.
Response to Chinese Office Action filed Oct. 24, 2014 with English translation for Chinese Application No. 201310064924.3; 27 pages.
European Extended Search Report dated Nov. 18, 2014 for European Application No. 11869957.8; 9 pages.
Notice of Allowance dated Nov. 18, 2014 for U.S. Appl. No. 13/987,326; 4 pages.
Letter from CCPIT Patent and Trademark Law Office dated Jan. 2, 2015 for Chinese Application No. 201310064924.3, 7 pages.
Chinese Office Action dated Nov. 17, 2014 for Chinese Application No. 201310064924.3, 3 pages.
Notice of Allowance dated Mar. 30, 2015 for U.S. Appl. No. 13/997,326; 7 pages.
Office Action dated Apr. 10, 2015 for U.S. Appl. No. 14/160,798; 8 pages.
European Search Report dated Apr. 17, 2015 for European Application No. 14197600.5; 7 pages.
Response to Office action with English translation filed Feb. 2, 2015 for Chinese Application No. 201310064924.3; 23 pages.
Response to Office action with English translation filed May 27, 2015 for Chinese Application No. 2001180072455.9; 15 pages.
Notification to Grant dated May 25, 2015 for Chinese Application No. 201310064924.3; 5 pages.
Notice of Allowance dated Apr. 23, 2015 for European Application No. 12187209.7; 39 pages.
Communication Pursuant to Rules 70(2) and 70a(2) EPC and reference to Rule 39(1) EPC dated May 26, 2015 for European Application No. 14197698.5; 2 pages.
Image File Wrapper downloaded on May 21, 2015 for U.S. Appl. No. 14/041,494; 101 pages.
Response to Office Action filed on Oct. 23, 2014 for U.S. Appl. No. 13/957,326; 8 pages.
Office Action dated Aug. 6, 2014 for Chinese Application No. 201010624971.5; 17 pages.
Office Acton dated Jun. 26, 2014 for Australian Application No. 2010235901, 4 pages.
Response to office action flied Jun. 1, 2015 for European Application No. 11869957.8; 10 pages.

\* cited by examiner

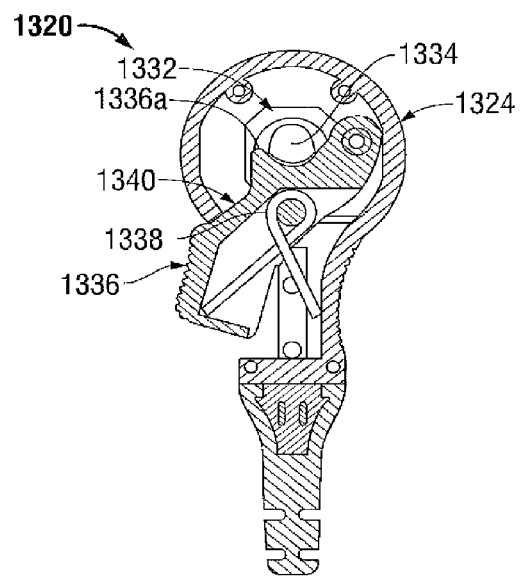
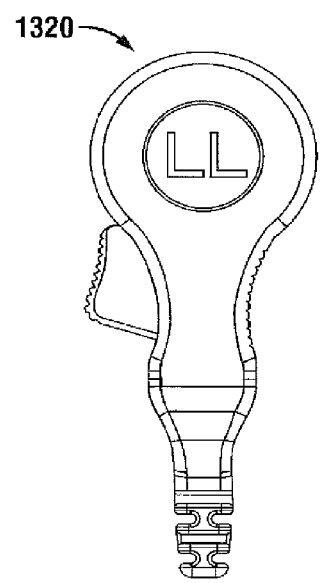
FIG. 13A  FIG. 13B
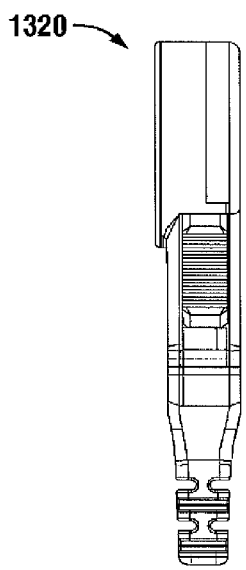
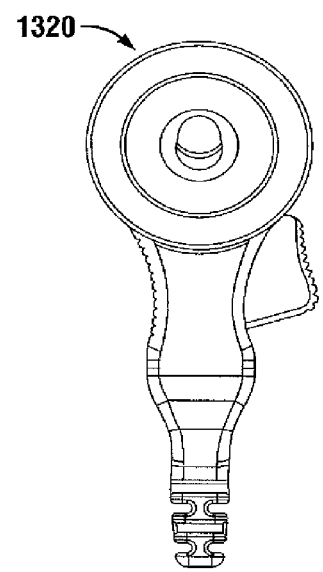
FIG. 13C  FIG. 13D

ECG ELECTRODE CONNECTOR

CROSS-REFERENCE TO RELATED APPLICATION

This application is a Continuation of U.S. patent application Ser. No. 14/041,471, filed on Sep. 30, 2013, which is a Continuation of U.S. patent application Ser. No. 13/785,713, filed on Mar. 5, 2013, now U.S. Pat. No. 8,690,611, which is a Continuation of U.S. patent application Ser. No. 13/443,096, filed on Apr. 10, 2012, now U.S. Pat. No. 8,408,948, which is a Continuation of U.S. patent application Ser. No. 13/182,656, filed on Jul. 14, 2011, now U.S. Pat. No. 8,152,571, which is a Continuation of U.S. patent application Ser. No. 12/330,550, filed on Dec. 9, 2008, now U.S. Pat. No. 8,038,484, which claims the benefit of and priority to U.S. Provisional Application No. 61/012,825, filed Dec. 11, 2007, the entirety of each of which is hereby incorporated by reference herein for all purposes.

BACKGROUND

1. Technical Field

The present disclosure relates to biomedical electrodes, and in particular, to a biomedical electrode connector for attaching a lead wire to an electrocardiogram (ECG) electrode placed on a patient's body.

2. Background of Related Art

Electrocardiograph (ECG) monitors are widely used to obtain medical (i.e. biopotential) signals containing information indicative of the electrical activity associated with the heart and pulmonary system. To obtain medical signals, ECG electrodes are applied to the skin of a patient in various locations. The electrodes, after being positioned on the patient, connect to an ECG monitor by a set of ECG lead wires. The distal end of the ECG lead wire, or portion closest to the patient, may include a connector which is adapted to operably connect to the electrode to receive medical signals from the body. The proximal end of the ECG lead set is operably coupled to the ECG monitor and supplies the medical signals received from the body to the ECG monitor.

A typical ECG electrode assembly may include an electrically conductive layer and a backing layer, the assembly having a patient contact side and a connector side. The contact side of the electrode pad may include biocompatible conductive gel or adhesive for affixing the electrode to a patient's body for facilitating an appropriate electrical connection between a patient's body and the electrode assembly. The connector side of the pad may incorporate a metallic press stud having a bulbous profile for coupling the electrode pad to the ECG lead wire. In use, the clinician removes a protective covering from the electrode side to expose the gel or adhesive, affixes the electrode pad to the patient's body, and attaches the appropriate ECG lead wire connector to the press stud by pressing or "snapping" the lead wire connector onto the bulbous press stud to achieve mechanical and electrical coupling of the electrode and lead wire. After use, a clinician then removes the ECG lead wire connector from the pad by pulling or "unsnapping" the connector from the pad.

The described ECG lead wire connector may have drawbacks. A clinician must apply considerable downward force on the lead wire connector to achieve positive engagement of the connector to the press stud. This high connecting force may cause additional and unnecessary discomfort or pain to the patient, whose existing medical condition may already be a source of discomfort or pain. A patient's discomfort may be compounded by the need to connect multiple electrodes which are customarily employed during ECG procedures.

Upon completion of the ECG procedure, a clinician must unsnap the ECG lead wire connector from the pad, which may further cause discomfort to the patient. In some instances, the connector does not readily disengage from the press stud thus requiring the clinician to use considerable upward force to unseat the connector. Often, these attempts to decouple the ECG lead wire connector from the electrode press stud will instead cause the pad to be suddenly and painfully torn from the patient's skin. In other instances, attempts to detach the ECG lead wire will cause the pad to become partially dislodged from the patient, which may impair the electrode's ability to receive biopotential signals. This is undesirable when, for example, the clinician wishes to detach the lead wires temporarily yet wishes to leave the pads in place to perform ECG testing on the patient at a future time.

In yet other instances, a snap lock connector may engage the press stud with insufficient force, which may cause suboptimal signal transmission from the electrode to the lead wire, as well as allowing the connector to be disengaged inadvertently by, for example, a slight tug on the lead wire. These effects are undesirable, because they may invalidate the ECG procedure, requiring time-consuming re-testing of the patient, or may lead to delayed, inaccurate or unreliable test results.

Additionally, the process of snapping and unsnapping lead wire connectors from ECG pads, while simultaneously striving to avoid the above-mentioned adverse effects, requires considerable manual dexterity on the part of the ECG clinician. Since clinicians typically repeat the electrode connection/disconnection routine many times each day, the described drawbacks may lead to clinician discontentment and fatigue.

SUMMARY

In an embodiment in accordance with the present disclosure, there is provided an ECG lead wire connector which includes a housing and a thumb cam lever having an open and a closed position. In the open position, the press stud of an ECG electrode assembly may be inserted into a mating receptacle provided in the housing, optionally using insignificant or no insertion force. Once placed in position, the thumb cam lever may be moved to the closed position, thereby positively coupling the press stud and connector without imparting undesirable force to the ECG electrode pad or to the patient. Detents may be provided by the disclosed lever to provide positive locking of the connector in the closed position to achieve optimal electrical coupling between the press stud and the connector, and additionally to provide tactile feedback to the clinician that the thumb cam lever is properly locked.

The connector may include a spring member which biases the thumb cam lever in the direction of the open position when the lever is unlocked. The spring member is configured to operably engage the narrow "waist" portion of the bulbous press stud when the thumb cam lever is in the closed position. When the thumb cam lever is in the closed position, the spring member biases the press stud against a mating electrical contact member provided within the connector housing to electrically couple the press stud and the contact member, and to achieve positive mechanical coupling of the press stud and the connector housing. The electrical contact member is operably coupled to the distal end of a lead wire by any suitable means, such as soldering, crimping, welding, or wire bonding. The proximal end of the lead wire may terminate in any suitable manner, such as to a connector, for operably coupling the lead wire to an ECG monitor. The lead wire may be supported at its exit point from the housing by a strain relief.

In another embodiment according to the present disclosure, an ECG lead wire connector is provided which includes a housing, and a pushbutton having an external face and an internal engaging surface. The pushbutton is biased by a spring member toward a locked position when released (i.e., when no pressure is applied to the pushbutton), and having an unlocked position when depressed (i.e., when sufficient pressure is applied to the face of the pushbutton by, for example, a clinician). A receptacle adapted to accept an electrode pad press stud is provided within the connector housing. When the pushbutton is depressed, the engaging surface thereof is configured to allow the insertion of a press stud into the receptacle, optionally using insignificant or no insertion force. Once the press stud is inserted, the pushbutton may be released, which causes the spring member to bias the engaging surface of the pushbutton against the press stud, engaging the press stud and a mating electrical contact member provided within the connector housing, to electrically couple the press stud and the contact member, and to achieve positive mechanical coupling of the press stud and the connector housing.

In one embodiment envisioned within the scope of the present disclosure, the pushbutton face may be positioned at the distal end of the connector housing. The spring member may be a coil spring positioned between the proximal end of the pushbutton and a corresponding saddle provided within the connector housing. The engaging surface is defined by an opening provided within the central portion of the pushbutton.

In another embodiment contemplated by the present disclosure, the pushbutton is a pivoting lever having at one end an external face positioned at the central region of the connector housing, and at the opposite end an engaging surface for engaging the press stud. The spring member may be a leaf spring positioned at the face end of the lever, between the housing and the lever, such that the lever face end is biased outwardly from the housing. Additionally or alternatively, the leaf spring may be positioned at the clamping end of the lever.

In the various embodiments, it is envisioned the electrical contact member provides a contact opening to receive the press stud. The opening may have narrow end and a wide end. For example, the opening may have an ovoid shape exhibiting one axis of symmetry ("egg-shaped"). Alternatively, the contact opening may be pear-shaped, keyhole-shaped, circular, or described by the intersection of two partially-coincident circles of differing radii. The opening may be dimensioned at its wide end to accept the bulbous press stud, optionally with insignificant or no interference. Conversely, the narrow end of the opening may be dimensioned to capture the narrow waist portion of the press stud. The contact opening may be configured such that, when engaged, the press stud is biased and/or clamped against the narrow end of the contact opening.

It should be understood that the spring members disclosed herein are not limited to coil and/or leaf springs, and may include any suitable source of biasing force, including without limitation gas springs, pressure- or vacuum-actuated devices, elastomeric springs, magnetic or electromagnetic devices, shape memory alloy motors, and other sources of biasing force as will be familiar to the skilled practitioner. Additionally or alternatively, the spring members may be integrally formed with, for example, the housing, lever, or pushbutton.

Other embodiments are envisioned within the present disclosure, such as an ECG lead wire connector having a plurality of pushbuttons, for example, that are disposed on opposite sides of the housing, wherein at least one button is operable to engage and disengage the press stud of an ECG pad.

Alternative modalities of press stud engagement are envisioned wherein, for example, the pushbutton operates in a push-on/push off fashion. In this arrangement, the connector is initially provided in an open or unlocked configuration. The press stud may then be inserted into the receptacle, optionally with insignificant or no insertion force. Once in place, the press stud may be engaged by pressing the pushbutton in a first push-on step. To disengage the press stud, the pushbutton is depressed a second time to release the press stud in a second push-off step and to reset the connector to the initial state, thereby readying the connector for subsequent use. In another modality of press stud engagement, the connector includes a source of biasing force, such as a spring member, that is configured to automatically engage a press stud upon detection of a triggering event, such as the insertion of a press stud into the connector. To disengage the press stud, a release control, such as a pushbutton or lever, is provided such that when said release control is actuated (i.e., pressed or moved), the press stud is released and/or ejected from the housing. It is further contemplated that actuating the release control resets the connector to the initial state, thereby readying the connector for subsequent use. Still other modalities of disengagement are contemplated where, for example, the press stud may be disengaged by pushing, pulling, twisting or otherwise moving the connector housing.

BRIEF DESCRIPTION OF THE DRAWINGS

Various embodiments of the presently disclosed ECG electrode connector are disclosed herein with reference to the drawings, wherein:

FIG. 13A is a schematic diagram of the FIG. 12A embodiment of an ECG electrode connector in accordance with the present disclosure;

FIG. 13B is a top view of the FIG. 12A embodiment of an ECG electrode connector in accordance with the present disclosure;

FIG. 13C is a side view of the FIG. 12A embodiment of an ECG electrode connector in accordance with the present disclosure; and FIG. 13D is a bottom view of the FIG. 12A embodiment of an ECG electrode connector in accordance with the present disclosure.

DETAILED DESCRIPTION OF EMBODIMENTS

Figure 2:
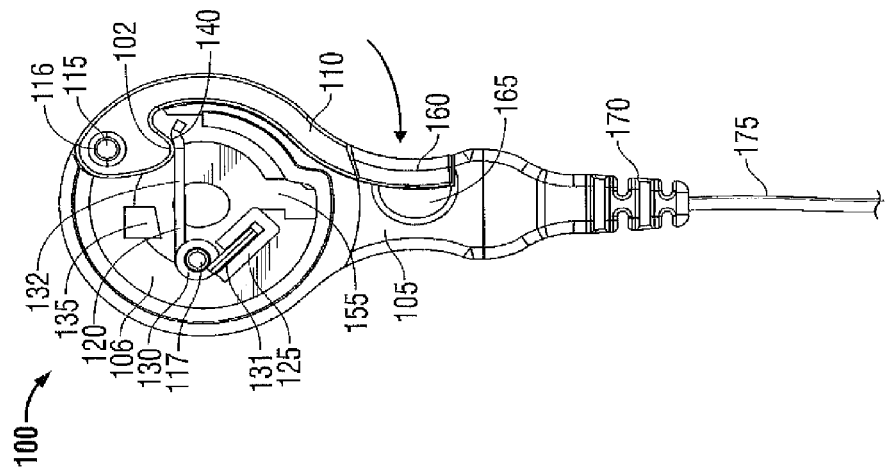
FIG. 2 illustrates the ECG connector of FIG. 1 having a thumb cam lever in a closed position in accordance with the present disclosure.

Embodiments of the presently disclosed ECG electrode connector and method are described herein in detail with reference to the drawings, in which like reference numerals designate identical or corresponding elements in each of the several views. As shown in the drawings and as described throughout the following description, and as is traditional when referring to relative positioning on an object, the term "proximal" refers to the end of the apparatus which is closer to the monitor and the term "distal" refers to the end of the apparatus which is further from the monitor. In the following description, well-known functions or constructions are not described in detail to avoid obscuring the present disclosure in unnecessary detail.

Figure 1:
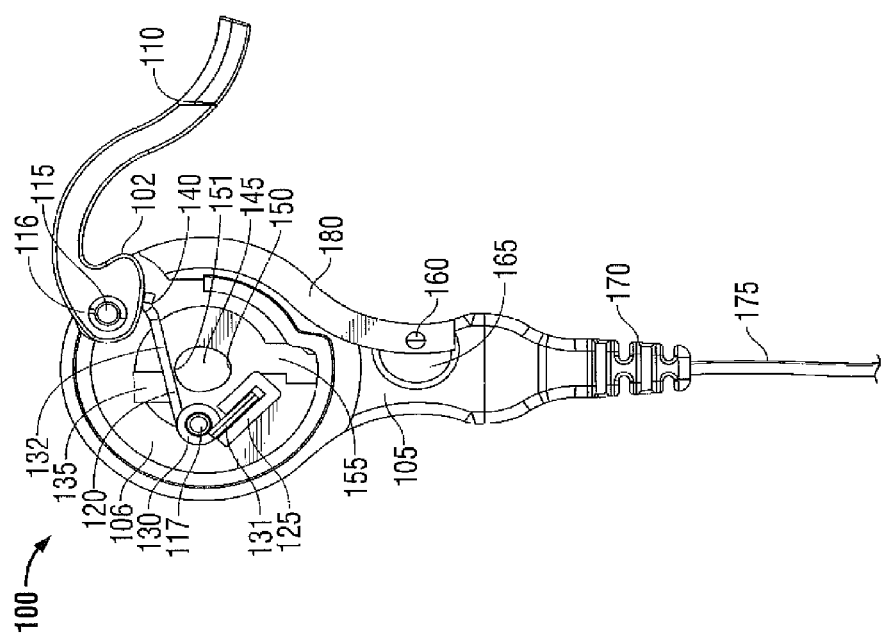
FIG. 1 is a schematic diagram of an embodiment of an ECG electrode connector in accordance with the present disclosure having a thumb cam lever in an open position.
Figure 3B:
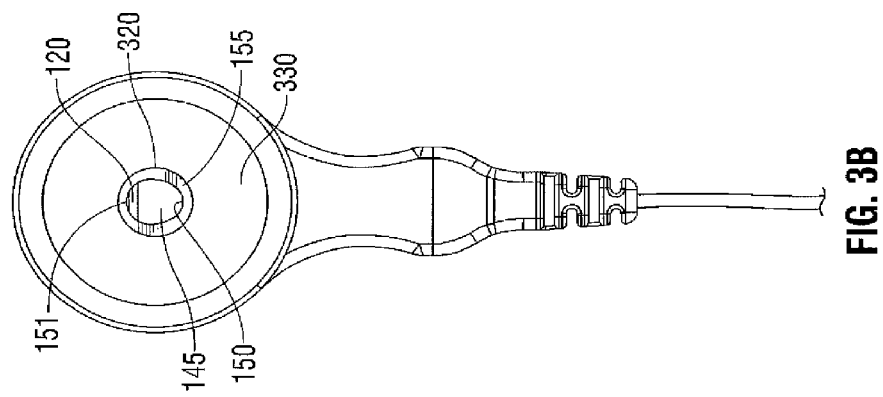
FIG. 3B is a bottom view of the FIG. 1 embodiment of an ECG electrode connector in accordance with the present disclosure.
Figure 3A:
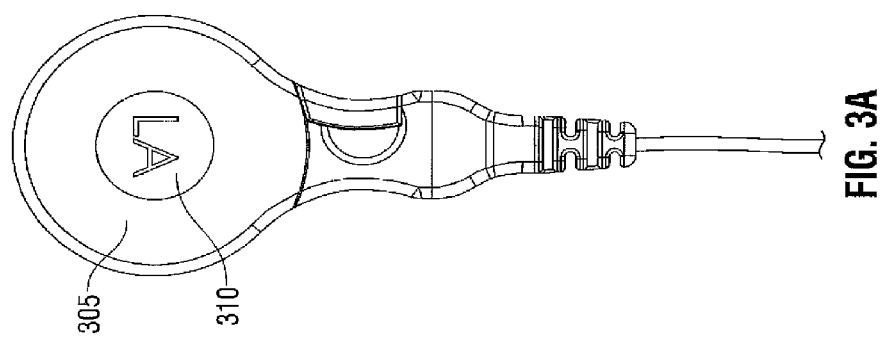
FIG. 3A is a top view of the FIG. 1 embodiment of an ECG electrode connector in accordance with the present disclosure.
Figure 3D:
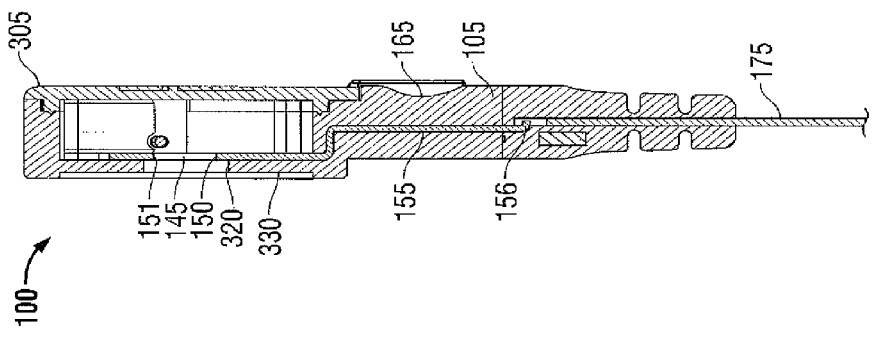
FIG. 3D is a side cutaway view of the FIG. 1 embodiment of an ECG electrode connector in accordance with the present disclosure.
Figure 3C:
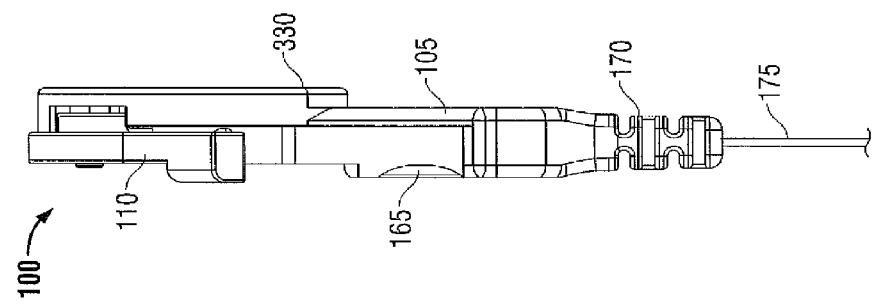
FIG. 3C is a side view of the FIG. 1 embodiment of an ECG electrode connector in accordance with the present disclosure.
Figure 3E:
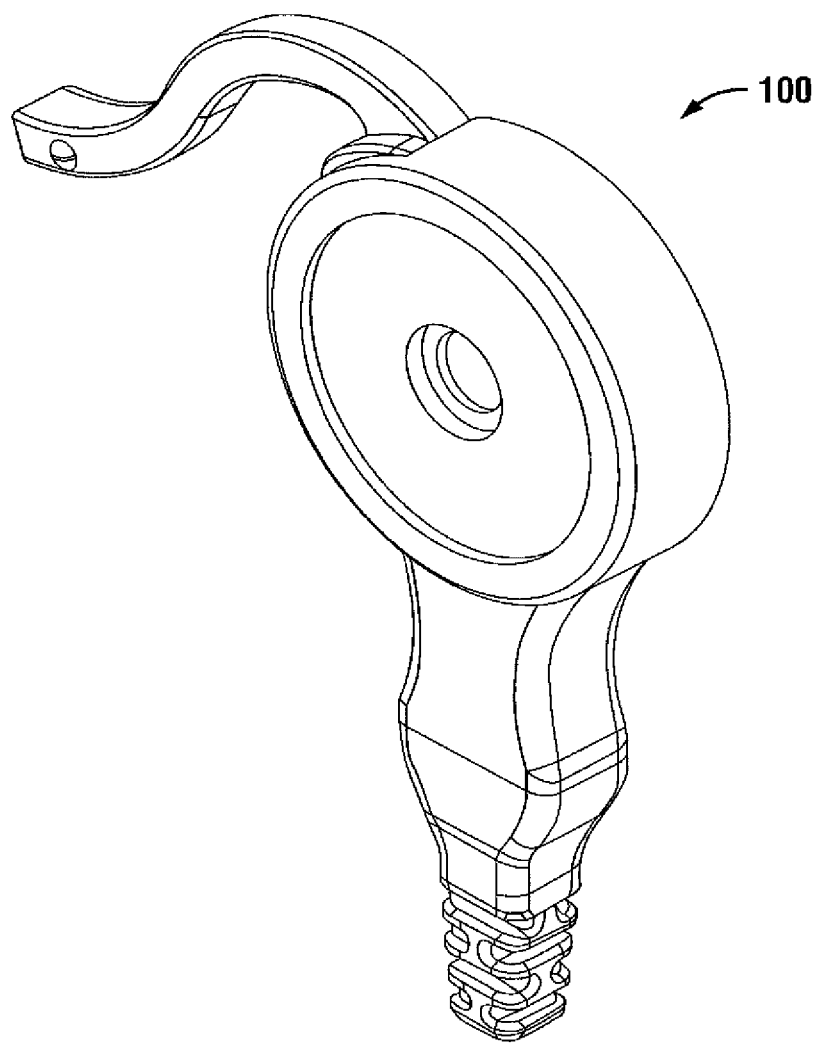
FIG. 3E is an oblique view of the FIG. 1 embodiment of an ECG electrode connector in accordance with the present disclosure.

Referring to FIGS. 1, 2, and 3A, there is shown an embodiment of an ECG electrode connector 100 having a thumb cam lever 110. The connector 100 includes a housing 105 that includes a cavity 106, a pivot pin 115, and a thumb cam lever 110 having a pivot hole 116 defined therein dimensioned to pivotably couple thumb cam lever 110 to pivot pin 115. Connector 100 may also include a cover 305 which optionally includes an identification marking 310 which may be incorporated with cover 305 by any suitable means, including without limitation printing, engraving, silk screening, stamping, or integrally molding said marking 310 onto cover 305. The housing 105, lever 110 and cover 305 may be constructed of any suitable non-conductive material, including without limitation any thermoplastic and/or elastomeric polymer such as polybutylene terephthalate (PBT), polyethylene terephthalate (PET), polyvinyl chloride (PVC), acrylonitrile butadiene styrene (ABS), thermoplastic polyurethanes (TPU), thermoplastic vulcanates (TPV), polypropylene (PP), polyethylene (PE), and/or fiber-reinforced polymer (FRP).

A V-spring 120 having a coil base 130, a fixed leg 131 and a movable leg 132 is coupled to housing 110 within cavity 106. Coil base 130 of V-spring 120 may be multi-turn, single-turn, or a V-shaped apex without a coil. V-spring 120 is retained at its base by pin 117 and is joined to housing 105 at its fixed end by saddle 125 such that movable leg 132 is biased in a distal direction, i.e., towards pivot pin 115. Additionally or alternatively, V-spring 120 may be joined to saddle 125 or cavity 106 by any suitable manner of bonding, such as by adhesive or heat welding. A stop 135 limits the outward flexure of movable leg 132. Thumb cam lever 110 includes a cam 102 which communicates with a detent 140 of spring member 120 when thumb cam lever 120 moves to a closed position, as shown in FIG. 2. Detent 140 and cam 102 cooperate to lock thumb cam lever 110 in a closed position, and additionally or alternatively, provide tactile feedback to a clinician. Additional locking and tactile feedback may be provided by the engagement of a lever detent 160 with a corresponding dimple (not shown) provided on thumb cam lever 110. A lever recess 180 may be provided by housing 105 to receive lever 110 when lever 110 is in the closed position. A finger recess 165 is provided on housing 105 to facilitate manipulation and/or grasping of thumb cam lever 110 by the clinician.

Connector 100 further includes an electrical contact member 155 which is disposed upon cavity 106. Contact member 155 may be constructed from any suitable electrically conductive material, including without limitation stainless steel or low-carbon steel. It is also envisioned contact member 155 may be constructed of a non-conductive material having a conductive coating. Contact member 155 is electrically coupled to a lead wire 175 by any suitable manner of connection, such as a crimp 156, or additionally or alternatively, soldering or wire bonding. Lead wire 175 may optionally be supported at its exit point from housing 105 by a strain relief 170. Contact member 155 provides a contact opening 145 defined therein to accept an electrical contact, such as a bulbous press stud of an ECG pad. In the embodiment, the contact opening 145 may be asymmetrical in shape, such as, for example, an ovoid shape dimensioned at its wide end 151 to accept the bulbous press stud, and dimensioned at its narrow end 150 to capture the narrow waist portion of the press stud. Referring now to FIGS. 3B, 3D, 10A and 10B, the bottom surface 330 of housing 105 provides an aperture 320 disposed therein which exposes contact opening 145 to the exterior of connector 100 to facilitate insertion of a press stud into the connector.

Figure 10A:
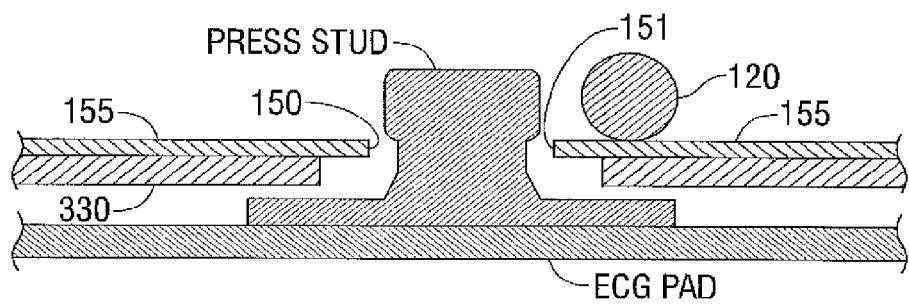
FIG. 10A is an exemplary side detail view of an ECG electrode connector in accordance with the present disclosure disengaged from a press stud of an ECG pad.
Figure 10B:
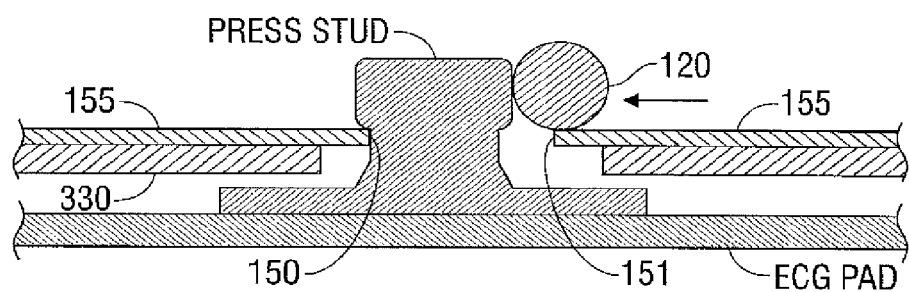
FIG. 10B is an exemplary side detail view of an ECG electrode connector in accordance with the present disclosure engaging a press stud of an ECG pad.
Figure 11B:
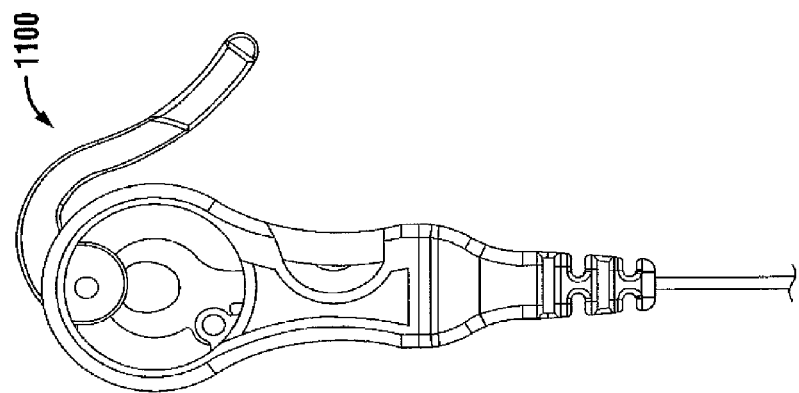
FIG. 11B illustrates the ECG connector of FIG. 11A having a thumb cam lever in an open position in accordance with the present disclosure.
Figure 11A:
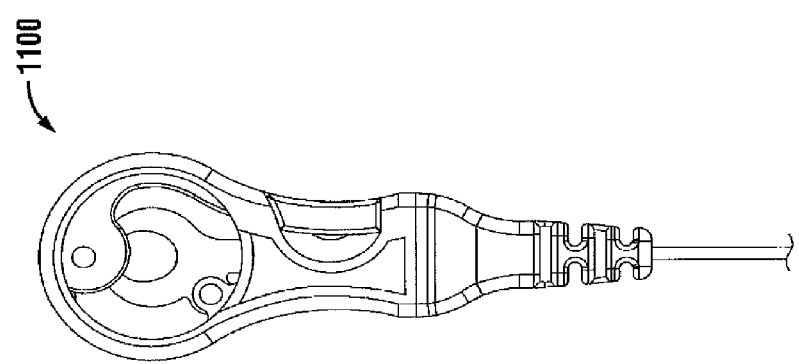
FIG. 11A is a schematic diagram of still another embodiment of an ECG electrode connector in accordance with the present disclosure having a thumb cam lever in a closed position.
Figure 12A:
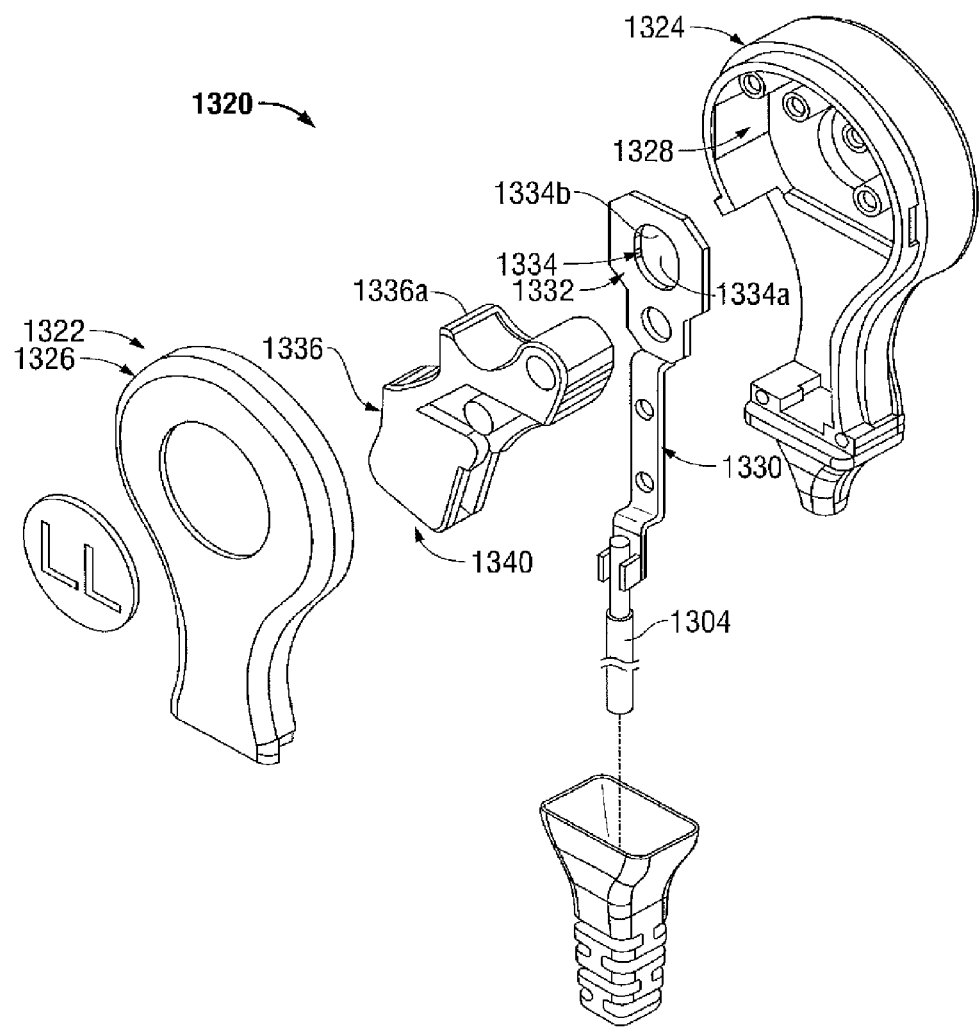
FIG. 12A is an exploded view of a yet another embodiment of an ECG electrode connector in accordance with the present disclosure.
Figure 12B:
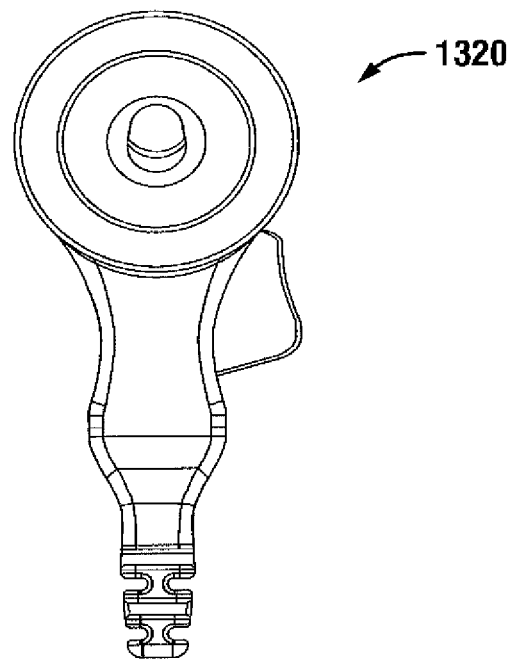
FIG. 12B is a bottom view of the FIG. 12A embodiment of an ECG electrode connector in accordance with the present disclosure.
Figure 12C:
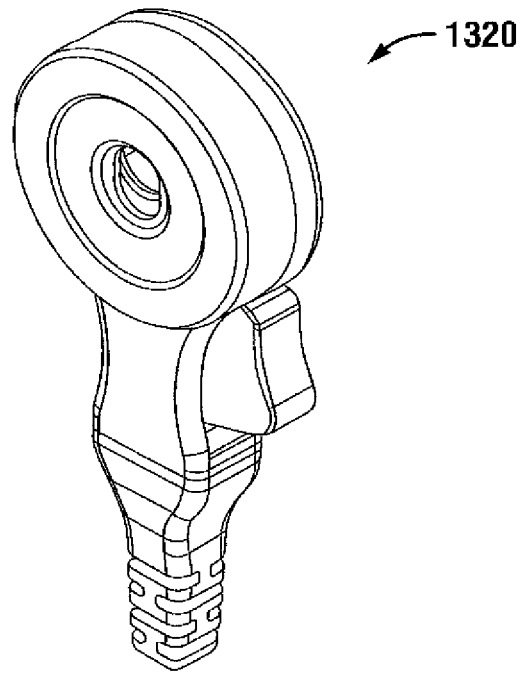
FIG. 12C is an oblique view of the FIG. 12A embodiment of an ECG electrode connector in accordance with the present disclosure.

Engaging a press stud into connector 100 may be accomplished by positioning lever 110 to an open position as shown in FIG. 1, whereupon cam 102 rotates away from detent 140, permitting movable leg 132 of V-spring 120 to flex distally and come to rest upon stop 135. A press stud may then be introduced into connector 100 by, for example, placing connector 100 over a press stud such that the bulbous end press stud is positioned within opening 145, as shown in FIG. 10A. Subsequent to insertion of the press stud, lever 110 may then be moved to the closed position as illustrated in FIG. 2, causing cam 102 to rotate towards moveable leg 132 of V-spring 120. The rotation of cam 102 causes it to ride over detent 140 thereby compressing movable leg 132 in a proximal direction, which mechanically engages and electrically couples the press stud with narrow end 150 of opening 145, as shown in FIG. 10B. Conversely, a press stud engaged with connector 100 as described may be disengaged by moving lever 110 from a closed position to an open position, causing cam 102 to rotate away from detent 140 and relax movable leg 132 of V-spring 120, which disengages the press stud and permits its removal as will be readily appreciated. In another embodiment as shown in FIGS. 11A and 11B in, an ECG electrode connector 1100 is provided wherein a cam is configured to cause mechanical engagement between the press stud and an electrical contact member. A spring may be added to facilitate the opening and actuation of the lever 110.

Turning now to FIGS. 4, 5, 6A, and 6B, another embodiment according to the present disclosure provides an ECG lead wire connector 400 that includes a housing 405 which provides a cavity 406, and a pushbutton 410 having an external face 411 and an internal engaging surface 432. Connector 400 may also include a cover 605 which optionally includes an identification marking 610 as previously described herein. Housing 405, pushbutton 410, cover 605 may be constructed from any suitable non-conductive material as previously described.

Pushbutton 410 is slidably disposed within housing 405 and is biased in a distal direction by a coil spring 420 that is retained at its distal (pushbutton) end by a saddle 426 provided by pushbutton 410, and at its proximal (housing) end by a saddle 425 provided by housing 405. Pushbutton 410 includes at least one stop member 436 which cooperates with stop members 435 and 437 provided within housing 405 to define the distal and proximal limits of travel, respectively, of pushbutton 410. Pushbutton 410 includes an opening 430 disposed therein having an engaging surface 432 for coupling the connector 400 to a press stud as will be further described below.

Connector 400 further includes an electrical contact member 455 which is disposed upon cavity 406. Contact member 455 is electrically coupled to a lead wire 475 by any suitable manner of connection as previously disclosed herein. Lead wire 475 may optionally be supported at its exit point from housing 405 by a strain relief 470. Contact member 455 provides a contact opening 445 defined therein to accept an electrical contact, such as a press stud, and may be an asymmetrical in shape as previously described herein, having a distal narrow end 450 and a proximal wide end 451. The bottom surface 630 of housing 405 provides an aperture 620 disposed therein which exposes contact opening 445 to the exterior of connector 400 to facilitate insertion of a press stud into the connector.

Figure 5:
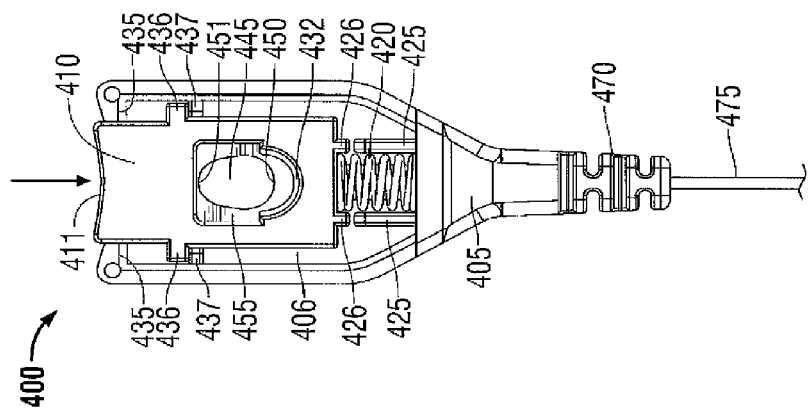
FIG. 5 illustrates the ECG connector of FIG. 4 having a pushbutton in a depressed position in accordance with the present disclosure.
Figure 4:
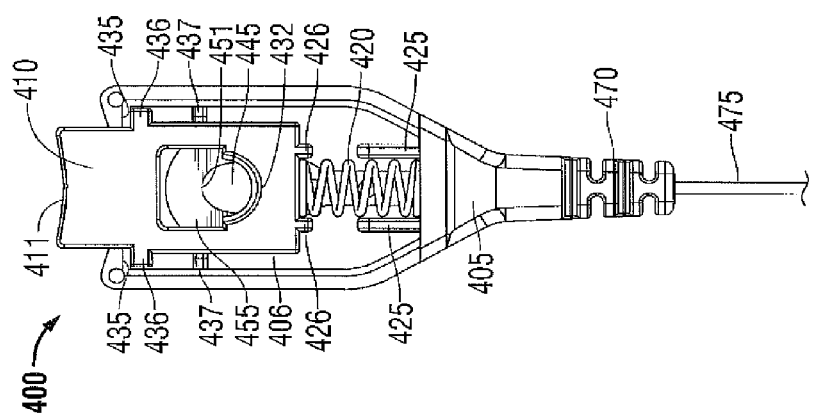
FIG. 4 is a schematic diagram of another embodiment of an ECG electrode connector in accordance with the present disclosure having a pushbutton in a released position.
Figure 6B:
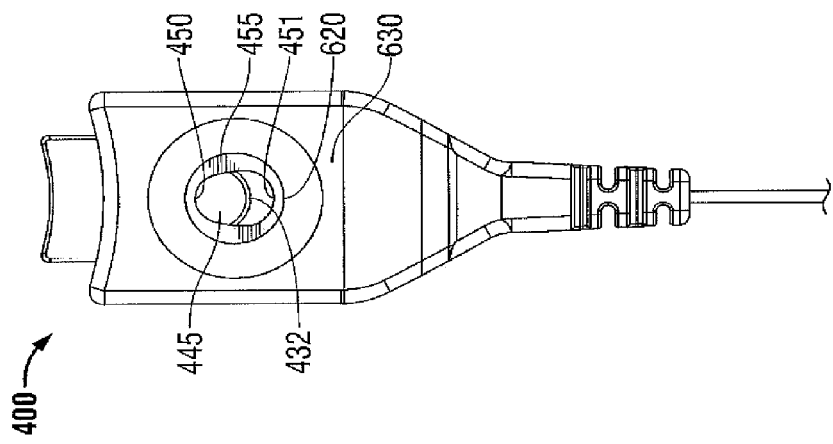
FIG. 6B is a bottom view of the FIG. 4 embodiment of an ECG electrode connector in accordance with the present disclosure.
Figure 6A:
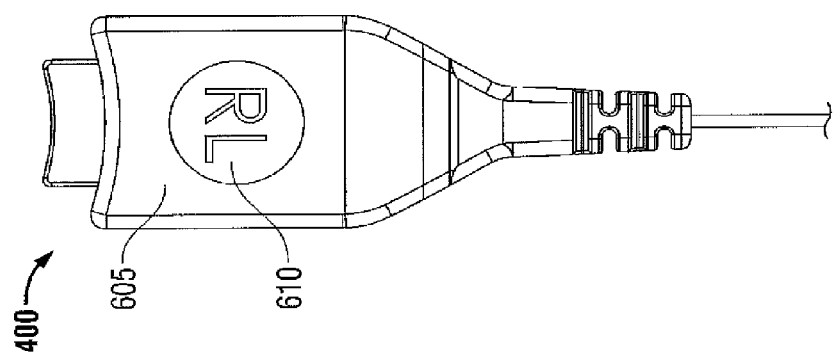
FIG. 6A is a top view of the FIG. 4 embodiment of an ECG electrode connector in accordance with the present disclosure.
Figure 6D:
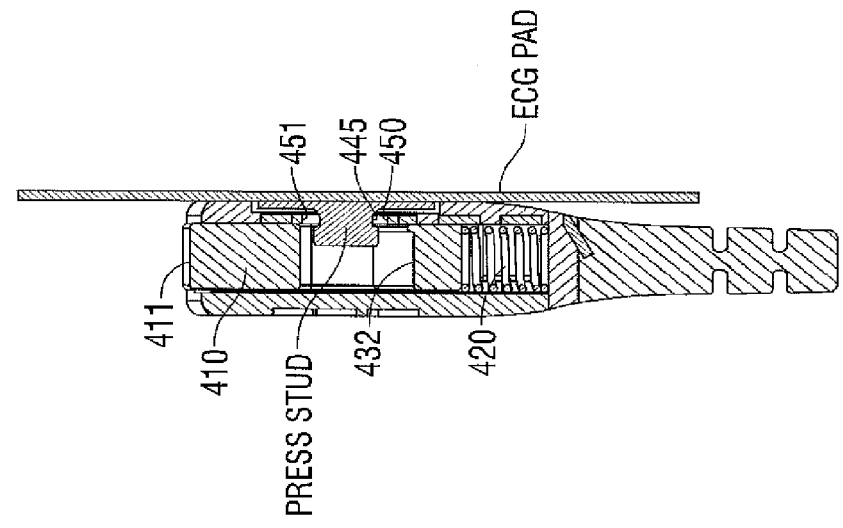
FIG. 6D is a side cutaway view of the FIG. 4 embodiment of an ECG electrode connector having a pushbutton in a depressed position in accordance with the present disclosure.
Figure 6C:
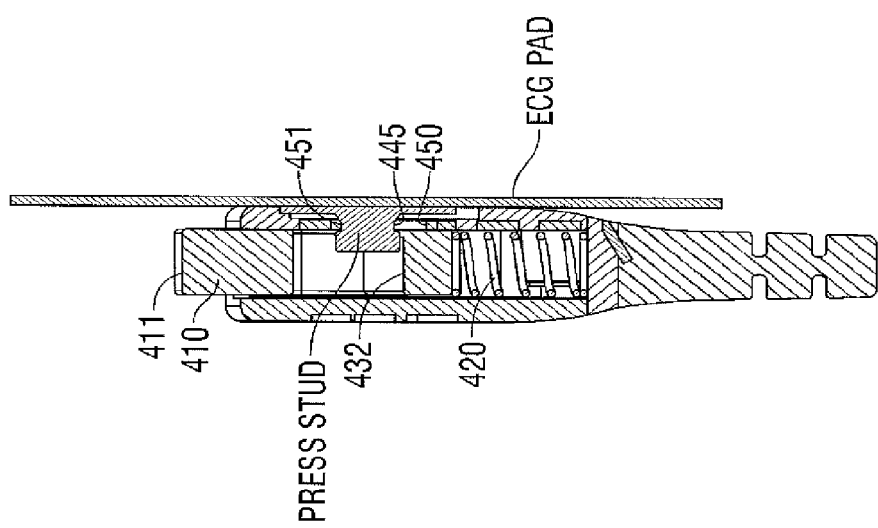
FIG. 6C is a side cutaway view of the FIG. 4 embodiment of an ECG electrode connector having a pushbutton in a released position in accordance with the present disclosure.

Engaging a press stud into connector 400 may be accomplished by depressing pushbutton 410, by, for example, applying sufficient finger pressure to pushbutton face 411 so as to overcome the bias of coil spring 420, thereby moving pushbutton 410 from a distal locked position as shown in FIG. 4 to a proximal open position as shown in FIG. 5. Opening 430 correspondingly moves proximally, exposing the wide proximal end 451 of contact opening 445 and facilitating the insertion of a press stud into connector 400 as best shown in FIG. 6D. Subsequent to insertion of a press stud, pushbutton 410 may then be released whereupon the biasing force of coil spring 420 causes pushbutton 410 to move distally, causing engaging surface 432 to mechanically engage and electrically couple the press stud with narrow end 450 of contact opening 445, as best shown in FIG. 6C. Conversely, a press stud engaged with connector 400 as described may be disengaged by depressing pushbutton 410, causing engaging surface 432 to move proximally, releasing the press stud and facilitating its removal from connector 400. Upon removal of the press stud, pushbutton 410 may be released, readying connector 400 for subsequent use. It is also contemplated in this embodiment to add components, such as linkages or gearing, between pushbutton and electrical contact member to achieve mechanical advantage and improved clamping or connection force.

Yet another embodiment in accordance with the present disclosure is described with reference to FIGS. 7, 8, 9A, and 9B, wherein is shown an ECG lead wire connector 700 having a housing 705 which provides a cavity 706, and a lever 710 pivotally disposed thereupon having an actuating end 715, an external pushbutton face 711, a pivot 712, and an engaging region 716. Connector 700 may also include a cover 905 which optionally includes an identification marking 910 as previously described herein. Housing 705, lever 710, and cover 605 may be constructed from any suitable non-conductive material as previously described herein.

Figure 7:
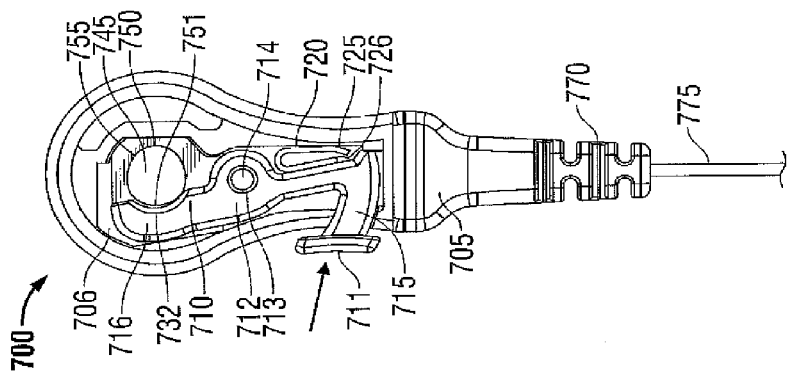
FIG. 7 is a schematic diagram of yet another embodiment of an ECG electrode connector in accordance with the present disclosure having a pivoting lever pushbutton in a released position.
Figure 8:
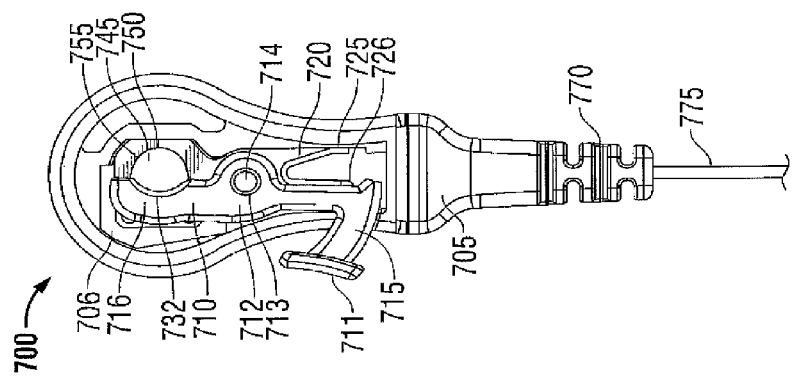
FIG. 8 illustrates the ECG connector of FIG. 7 having a pivoting lever pushbutton in a depressed position in accordance with the present disclosure.

As shown in FIGS. 7 and 8, lever 710 includes a pivot hole 713 disposed therein for pivotally engaging a pivot pin 714 that is provided by housing 705. Actuation end 715 of lever 710 is biased in an outward direction by a leaf spring 720 that is retained at its lever end by surface 726 of lever 710, and at its housing end by a surface 725 of housing 705. Additionally or alternatively, leaf spring 720 may include at least one tab (not shown) retained by at least one slot (not shown) provided by lever surface 726 and/or housing surface 725. Engaging region 716 of lever 710 includes an engaging surface 732 for coupling the connector 700 to a press stud as will be further described below.

Figure 9B:
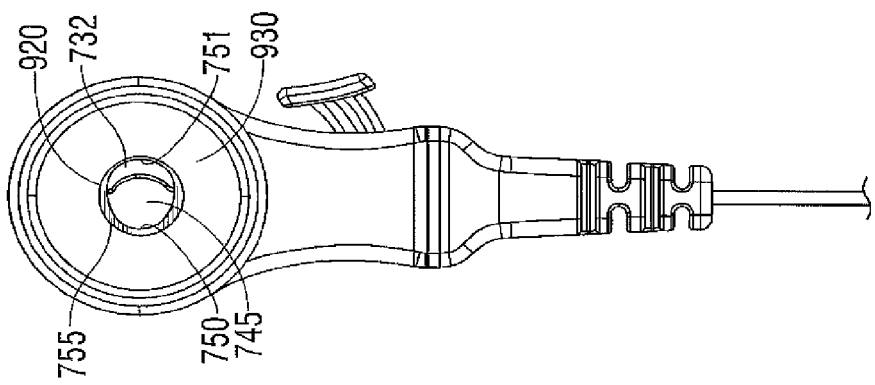
FIG. 9B is a bottom view of the FIG. 7 embodiment of an ECG electrode connector in accordance with the present disclosure.
Figure 9A:
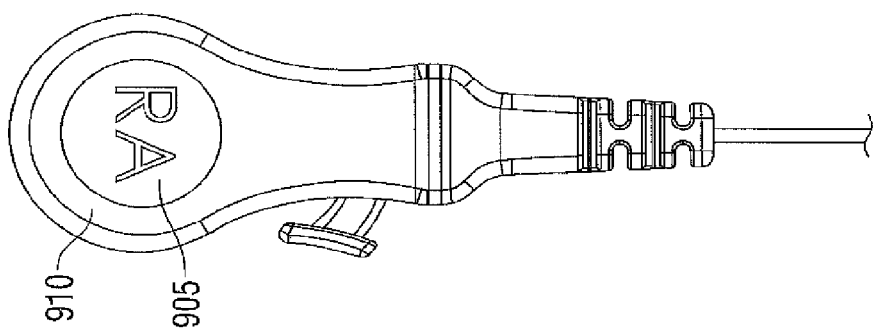
FIG. 9A is a top view of the FIG. 7 embodiment of an ECG electrode connector in accordance with the present disclosure.
Figure 9D:
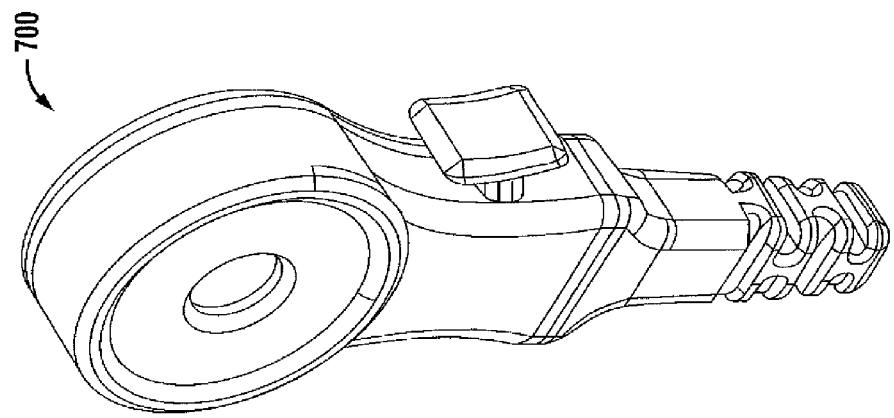
FIG. 9D is an oblique view of the FIG. 7 embodiment of an ECG electrode connector in accordance with the present disclosure.
Figure 9C:
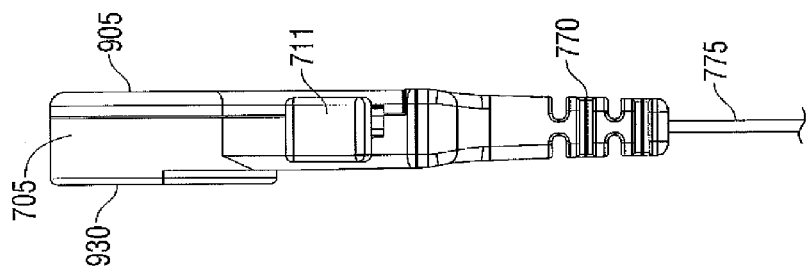
FIG. 9C is a side view of the FIG. 7 embodiment of an ECG electrode connector in accordance with the present disclosure.

Connector 700 further includes an electrical contact member 755 which is disposed upon cavity 706. Contact member 755 is electrically coupled to a lead wire 775 by any suitable manner of connection as previously disclosed herein. Lead wire 775 may optionally be supported at its exit point from housing 705 by a strain relief 770. Contact member 755 provides a contact opening 745 defined therein to accept an electrical contact, such as a press stud, and may be an asymmetrical in shape as previously described herein, having a narrow end 750 and a wide end 751 as best illustrated in FIGS. 8 and 9B. The bottom surface 930 of housing 705 provides an aperture 920 disposed therein which exposes contact opening 745 to the exterior of connector 700 to facilitate insertion of a press stud into the connector.

Engaging a press stud into connector 700 may be accomplished by depressing pushbutton face 711, by, for example, applying sufficient finger pressure thereto so as to overcome the bias of leaf spring 720, thereby causing engaging region 716 of lever 710 to swing from a closed position as shown in FIG. 7 to an open position as shown in FIG. 8. The wide end 751 of contact opening 745 is thereby exposed thus facilitating the insertion of a press stud into connector 700. Pushbutton face 711 may then be released whereupon the biasing force of leaf spring 720 causes engaging surface 732 to move toward the inserted press stud to mechanically engage and electrically couple the press stud with narrow end 750 of contact opening 745, as will be readily appreciated. Conversely, a press stud engaged with connector 700 as described may be disengaged by depressing pushbutton 710, causing engaging surface 732 to swing away from the press stud (i.e., away from narrow end 750 of contact opening 745), releasing the press stud and facilitating its removal from connector 700. Upon removal of the press stud, pushbutton face 711 may then be released, readying connector 700 for subsequent use.

With reference now to FIGS. 12A-C and FIGS. 13A-D, an embodiment of an ECG electrode connector 1320 includes a housing 1322 having an upper member 1324 and a lower member 1326, and defining an internal cavity 1328 therebetween. Housing 1322 is fabricated from a non-conducting material, e.g., an injection molded polymer which electrically insulates the subject from the conductive element(s) therewithin. Upper member 1324 and lower member 1326 are separate components attached to each other by any suitable method of bonding, such as without limitation, adhesive, ultrasonic welding, or heat welding. Upper member 1324 and lower member 1326 form a non-conductive element of the housing 1322.

Housing 1322 includes a lead wire terminal 1330 which is electrically connected to a respective end of lead wire 1304 by any suitable method of connection, including without limitation, crimping, soldering, or welding. Housing 1322 supports a contact member 1332 that is electrically connected to lead wire terminal 1330. Contact member 1332 and lead wire terminal 1330 may be integrally formed. Contact member 1332 defines a contact opening 1334 formed therein and in communication with internal cavity 1328 of housing 1322. Contact opening 1334 includes first contact opening portion 1334a and second contact opening portion 1334b. First contact opening portion 1334a defines an internal dimension or diameter which is greater than the corresponding internal dimension or diameter of second contact opening portion 1334b.

Housing 1322 further includes a lever 1340 pivotably connected thereto. Lever 1340 includes an actuating end 1336. Lever 1340 is biased to a first position by a biasing member 1338. Lever 1340 includes an engaging region 1336a projecting therefrom so as to extend across first contact opening portion 1334a of contact opening 1334 when lever 1340 is in the first position. In use, lever 1340 is actuatable to a second position wherein engaging region 1336a thereof does not obstruct or extend across first contact opening portion 1334a of contact opening 1334. For example, a clinician may apply finger pressure to actuating end 1336 that is sufficient to overcome the biasing force of biasing member 1338, thereby causing engaging region 1336a to move to a second position as herein described.

ECG electrode connector 1320 is adapted for connection to a conventional snap-type biomedical electrode (not explicitly shown). A typical snap-type biomedical electrode incorporates an electrode flange or base and male press stud or terminal extending in transverse relation to the electrode base. The male press stud terminal may have a bulbous head whereby an upper portion of the terminal has a greater cross-sectional dimension than a lower portion of the terminal. Accordingly, in use, when lever 1340 of electrode connector 1320 is in the second position, the head of the male press stud terminal of the snap-type biomedical electrode may be inserted into first contact opening portion 1334a of contact opening 1334 and actuating end 1336, and thus, lever 1340, may be released so that biasing member 1338 moves engaging region 1336a of lever 1340 against the head of the male press stud (not explicitly shown) to push or force the lower portion of the press stud into a second contact opening portion 1334b of contact opening 1334. The biasing force of biasing member 1338 helps to maintain the press stud within second contact opening portion 1334b of contact opening 1334 and thus inhibits removal or disconnection of the biomedical electrode from ECG connector 1320.

It will be understood that various modifications may be made to the embodiments disclosed herein. Further variations of the above-disclosed and other features and functions, or alternatives thereof, may be desirably combined into many other different systems, instruments and applications. Various presently unforeseen or unanticipated alternatives, modifications, variations or improvements therein may be subsequently made by those skilled in the art, which are also intended to be encompassed by the following claims.

What is claimed is:

1. An ECG connector assembly, comprising:
 a housing having an opening dimensioned to receive a press stud of an ECG electrode pad;
 an electrical contact member fixed to the housing and having a contact region disposed within the housing opening; and
 a pivotable lever having at least an engaged position and a disengaged position, wherein the lever comprises an actuating portion, an engaging region, and a pivot, the engaging region configured to operably engage the press stud to cause a portion of the press stud to contact the contact region of the electrical contact member when the lever is in the engaged position.

2. The ECG connector assembly of claim 1 wherein the engaging region is located between the pivot and the actuating portion.

3. The ECG connector assembly of claim 1 wherein the pivot is located between the engaging region and the actuating portion.

4. The ECG connector assembly of claim 1 further comprising a biasing member configured to bias the lever towards the engaged position.

5. The ECG connector assembly of claim 1 wherein the electrical contact member defines a contact plane and wherein the lever is pivotable about an axis orthogonal to the contact plane.

6. The ECG connector assembly of claim 1 wherein the contact region of the electrical contact member comprises a second opening smaller than and disposed at least partially within the housing opening.

7. The ECG connector assembly of claim 1 wherein the actuating portion of the lever protrudes through a lever recess defined in a sidewall of the housing when the lever is in the engaged position.

8. The ECG connector assembly of claim 7 further comprising:
 a detent provided within the lever recess; and
 a dimple, corresponding to the detent, provided on the lever, wherein the detent and the dimple engage to retain the lever when the lever is in the disengaged position.

9. The ECG connector assembly of claim 1 further comprising:
- a lead wire coupled to the electrical contact member; and
- a strain relief having at least a portion of the lead wire disposed therethrough.

10. The ECG connector assembly of claim 1 wherein the housing and the lever are constructed from an electrically non-conducting material.

11. A method of engaging a press stud of an ECU electrode pad with an ECG connector, comprising:
- providing the ECG connector having a housing with an opening dimensioned to receive the press stud of an ECG electrode pad, an electrical contact member secured to the housing and having a contact region accessible through the housing opening, and a lever having an actuating portion, an engaging region, and a pivot;
- positioning the actuating portion of the lever in a disengaged position;
- introducing the press stud into the housing opening; and
- positioning the actuating portion of the lever in an engaged position in which the engaging region engages the press stud to cause at least a portion of the press stud to contact the contact region of the electrical contact member.

12. The method of claim 11 further comprising providing a bias member within the housing, wherein positioning the actuating portion of the lever in the engaged position comprises applying a bias force to the lever with the bias member.

13. The method of claim 12 wherein positioning the actuating portion of the lever in the disengaged position comprises applying a pressure to the actuating portion to overcome the bias force.

* * * * *